(12) United States Patent
Vozila

(10) Patent No.: US 11,270,261 B2
(45) Date of Patent: Mar. 8, 2022

(54) SYSTEM AND METHOD FOR CONCEPT FORMATTING

(71) Applicant: Nuance Communications, Inc., Burlington, MA (US)

(72) Inventor: Paul Joseph Vozila, Arlington, MA (US)

(73) Assignee: NUANCE COMMUNICATIONS, INC., Burlington, MA (US)

( * ) Notice: Subject to any disclaimer, the term of this patent is extended or adjusted under 35 U.S.C. 154(b) by 273 days.

(21) Appl. No.: 16/270,782

(22) Filed: Feb. 8, 2019

(65) Prior Publication Data

US 2019/0272827 A1    Sep. 5, 2019

Related U.S. Application Data

(60) Provisional application No. 62/638,809, filed on Mar. 5, 2018.

(51) Int. Cl.
*G16H 15/00* (2018.01)
*G10L 15/22* (2006.01)
(Continued)

(52) U.S. Cl.
CPC ............ *G06Q 10/10* (2013.01); *G06F 3/165* (2013.01); *G06F 40/117* (2020.01); *G06F 40/30* (2020.01); *G06T 7/20* (2013.01); *G10L 15/22* (2013.01); *G10L 15/26* (2013.01); *G10L 15/30* (2013.01); *G10L 25/45* (2013.01); *G10L 25/51* (2013.01); *G16H 10/20* (2018.01); *G16H 10/40* (2018.01); *G16H 10/60* (2018.01); *G16H 15/00* (2018.01);
(Continued)

(58) Field of Classification Search
CPC ............................... G16H 15/00; G10L 15/22
See application file for complete search history.

(56) References Cited

U.S. PATENT DOCUMENTS 5,805,747 A    9/1998  Bradford
5,809,476 A    9/1998  Ryan
(Continued)

FOREIGN PATENT DOCUMENTS

CN    101790752 A    7/2010
CN    106448722 A    2/2017
(Continued)

OTHER PUBLICATIONS

Non-Final Office Action issued in related U.S. Appl. No. 16/271,616 dated Nov. 15, 2019.
(Continued)

*Primary Examiner* — Bryan S Blankenagel
(74) *Attorney, Agent, or Firm* — Brian J. Colandreo; Michael T. Abramson; Holland & Knight LLP

(57) ABSTRACT

A method, computer program product, and computer system for mapping, by a computing device, an automatic speech recognition output of a conversation to a concept marker and a verbalized version of a value associated with the concept marker based upon, at least in part, the automatic speech recognition output of the conversation. The concept marker and the verbalized version of the value associated with the concept marker may be replaced with a formatted version. A plurality of user selectable format configurations of the formatted version may be provided as a textual output in a user interface.

15 Claims, 9 Drawing Sheets

(51) Int. Cl.

| | |
|---|---|
| *G06Q 10/10* | (2012.01) |
| *G10L 25/51* | (2013.01) |
| *G06F 3/16* | (2006.01) |
| *G10L 25/45* | (2013.01) |
| *G16H 10/20* | (2018.01) |
| *G06T 7/20* | (2017.01) |
| *H04R 1/40* | (2006.01) |
| *H04R 3/00* | (2006.01) |
| *G10L 15/30* | (2013.01) |
| *G16H 10/40* | (2018.01) |
| *G16H 10/60* | (2018.01) |
| *G16H 50/70* | (2018.01) |
| *G10L 15/26* | (2006.01) |
| *G06F 40/30* | (2020.01) |
| *G06F 40/117* | (2020.01) |

(52) U.S. Cl.
CPC ............ *G16H 50/70* (2018.01); *H04R 1/406* (2013.01); *H04R 3/005* (2013.01); *G06T 2207/30196* (2013.01)

(56) References Cited

U.S. PATENT DOCUMENTS

| | | | |
|---|---|---|---|
| 5,940,118 A | | 8/1999 | Van Schyndel |
| 5,970,455 A | | 10/1999 | Wilcox et al. |
| 5,970,457 A | | 10/1999 | Brant et al. |
| 6,004,276 A | * | 12/1999 | Wright .................. G06F 19/322 |
| | | | 128/923 |
| 6,031,526 A | | 2/2000 | Shipp |
| 6,266,635 B1 | | 7/2001 | Sneh |
| 6,332,122 B1 | | 12/2001 | Ortega et al. |
| 6,401,063 B1 | | 6/2002 | Hebert et al. |
| 6,405,165 B1 | | 6/2002 | Blum et al. |
| 6,434,520 B1 | | 8/2002 | Kanevsky et al. |
| 6,523,166 B1 | | 2/2003 | Mishra et al. |
| 6,589,169 B1 | | 7/2003 | Surwit et al. |
| 6,801,916 B2 | | 10/2004 | Roberge et al. |
| 6,823,203 B2 | | 11/2004 | Jordan |
| 6,847,336 B1 | | 1/2005 | Lemelson et al. |
| 6,915,254 B1 | | 7/2005 | Heinze et al. |
| 7,236,618 B1 | | 6/2007 | Chui et al. |
| 7,298,930 B1 | | 11/2007 | Erol |
| 7,412,396 B1 | | 8/2008 | Haq |
| 7,493,253 B1 | | 2/2009 | Ceusters et al. |
| 7,496,500 B2 | | 2/2009 | Reed et al. |
| 7,516,070 B2 | | 4/2009 | Kahn |
| 7,558,156 B2 | | 7/2009 | Vook et al. |
| 7,817,805 B1 | | 10/2010 | Griffin |
| 7,830,962 B1 | | 11/2010 | Fernandez |
| 8,214,082 B2 | | 7/2012 | Tsai et al. |
| 8,345,887 B1 | | 1/2013 | Betbeder |
| 8,369,593 B2 | | 2/2013 | Peng et al. |
| 8,589,177 B2 | | 11/2013 | Haq |
| 8,589,372 B2 | | 11/2013 | Krislov |
| 8,606,594 B2 | | 12/2013 | Stern et al. |
| 8,661,012 B1 | | 2/2014 | Baker et al. |
| 8,843,372 B1 | | 9/2014 | Isenberg |
| 8,983,889 B1 | | 3/2015 | Stoneman |
| 9,146,301 B2 | | 9/2015 | Adcock et al. |
| 9,224,180 B2 | | 12/2015 | Macoviak et al. |
| 9,270,964 B1 | | 2/2016 | Tseytlin |
| 9,293,151 B2 | | 3/2016 | Herbig et al. |
| 9,326,143 B2 | | 4/2016 | McFarland |
| 9,338,493 B2 | | 10/2016 | Van Os et al. |
| 9,536,049 B2 | | 1/2017 | Brown et al. |
| 9,536,106 B2 | | 1/2017 | Fram |
| 9,569,593 B2 | | 2/2017 | Casella dos Santos |
| 9,569,594 B2 | | 2/2017 | Casella dos Santos |
| 9,668,006 B2 | | 5/2017 | Betts et al. |
| 9,668,024 B2 | | 5/2017 | Os et al. |
| 9,668,066 B1 | | 5/2017 | Betts et al. |
| 9,679,102 B2 | | 6/2017 | Cardoza et al. |
| 9,779,631 B1 | | 10/2017 | Miller et al. |
| 9,785,753 B2 | | 10/2017 | Casella dos Santos |
| 9,799,206 B1 | | 10/2017 | Wilson Van Horn et al. |
| 9,824,691 B1 | | 11/2017 | Montero et al. |
| RE47,049 E | | 9/2018 | Zhu |
| 10,090,068 B2 | | 10/2018 | Kusens et al. |
| 10,219,083 B2 | | 2/2019 | Farmani et al. |
| 10,423,948 B1 | | 9/2019 | Wilson et al. |
| 10,440,498 B1 | | 10/2019 | Amengual Gari et al. |
| 10,491,598 B2 | | 11/2019 | Leblang et al. |
| 10,559,295 B1 | | 2/2020 | Abel |
| 10,693,872 B1 | | 6/2020 | Larson et al. |
| 10,719,222 B2 | | 7/2020 | Strader |
| 10,785,565 B2 | | 9/2020 | Mate et al. |
| 10,810,574 B1 | | 10/2020 | Wilson et al. |
| 10,972,682 B1 | | 4/2021 | Muenster |
| 2001/0029322 A1 | | 10/2001 | Iliff |
| 2001/0041992 A1 | | 11/2001 | Lewis et al. |
| 2001/0042114 A1 | | 11/2001 | Agraharam et al. |
| 2002/0032583 A1 | | 3/2002 | Joao |
| 2002/0069056 A1 | | 6/2002 | Nofsinger |
| 2002/0072896 A1 | | 6/2002 | Roberge et al. |
| 2002/0082825 A1 | | 6/2002 | Rowlandson et al. |
| 2002/0143533 A1 | | 10/2002 | Lucas et al. |
| 2002/0170565 A1 | | 11/2002 | Walker et al. |
| 2002/0178002 A1 | | 11/2002 | Boguraev et al. |
| 2002/0194005 A1 | | 12/2002 | Lahr |
| 2003/0028401 A1 | | 2/2003 | Kaufman et al. |
| 2003/0105638 A1 | | 6/2003 | Taira |
| 2003/0125940 A1 | | 7/2003 | Basson et al. |
| 2003/0154085 A1 | | 8/2003 | Kelley |
| 2003/0185411 A1 | | 10/2003 | Atlas et al. |
| 2003/0216937 A1 | | 11/2003 | Schreiber et al. |
| 2004/0078228 A1 | | 4/2004 | Fitzgerald et al. |
| 2004/0122701 A1 | | 6/2004 | Dahlin |
| 2004/0128323 A1 | | 7/2004 | Walker |
| 2004/0162728 A1 | | 8/2004 | Thomson et al. |
| 2004/0167644 A1 | | 8/2004 | Swinney |
| 2004/0172070 A1 | | 9/2004 | Moore et al. |
| 2004/0186712 A1 | | 9/2004 | Coles et al. |
| 2004/0243545 A1 | | 12/2004 | Boone et al. |
| 2004/0247016 A1 | * | 12/2004 | Faries, Jr. ............... A61B 50/13 |
| | | | 374/162 |
| 2005/0055215 A1 | | 3/2005 | Klotz |
| 2005/0075543 A1 | | 4/2005 | Calabrese |
| 2005/0114179 A1 | | 5/2005 | Brackett et al. |
| 2005/0165285 A1 | | 7/2005 | Liff |
| 2005/0192848 A1 | | 9/2005 | Kozminski et al. |
| 2006/0041427 A1 | | 2/2006 | Yegnanarayanan et al. |
| 2006/0041428 A1 | | 2/2006 | Fritsch et al. |
| 2006/0074656 A1 | | 4/2006 | Mathias et al. |
| 2006/0092978 A1 | | 5/2006 | John et al. |
| 2006/0104454 A1 | | 5/2006 | Guitarte Perez et al. |
| 2006/0104458 A1 | | 5/2006 | Kenoyer et al. |
| 2006/0142739 A1 | | 6/2006 | DiSilestro et al. |
| 2006/0173753 A1 | | 8/2006 | Padmanabhan et al. |
| 2006/0241943 A1 | | 10/2006 | Benja-Athon et al. |
| 2006/0277071 A1 | | 12/2006 | Shufeldt |
| 2007/0033032 A1 | | 2/2007 | Schubert et al. |
| 2007/0071206 A1 | | 3/2007 | Gainsboro et al. |
| 2007/0136218 A1 | | 6/2007 | Bauer et al. |
| 2007/0167709 A1 | | 7/2007 | Slayton et al. |
| 2007/0169021 A1 | * | 7/2007 | Huynh .................. G16H 15/00 |
| | | | 717/136 |
| 2007/0208567 A1 | | 9/2007 | Amento et al. |
| 2007/0233488 A1 | | 10/2007 | Carus et al. |
| 2007/0260977 A1 | | 11/2007 | Allard et al. |
| 2008/0004505 A1 | | 1/2008 | Kapit et al. |
| 2008/0004904 A1 | | 1/2008 | Tran |
| 2008/0040162 A1 | | 2/2008 | Brice |
| 2008/0059182 A1 | | 3/2008 | Benja-Athon et al. |
| 2008/0062280 A1 | | 3/2008 | Wang et al. |
| 2008/0071575 A1 | | 3/2008 | Climax et al. |
| 2008/0177537 A1 | | 7/2008 | Ash et al. |
| 2008/0240463 A1 | | 10/2008 | Florencio et al. |
| 2008/0247274 A1 | | 10/2008 | Seltzer et al. |
| 2008/0263451 A1 | | 10/2008 | Portele et al. |
| 2008/0285772 A1 | | 11/2008 | Haulick et al. |
| 2009/0024416 A1 | | 1/2009 | McLaughlin et al. |

(56) References Cited

U.S. PATENT DOCUMENTS

| | | | |
|---|---|---|---|
| 2009/0055735 A1* | 2/2009 | Zaleski | G16H 40/63 715/700 |
| 2009/0070103 A1 | 3/2009 | Beggelman et al. | |
| 2009/0089100 A1 | 4/2009 | Nenov et al. | |
| 2009/0136094 A1 | 5/2009 | Driver | |
| 2009/0150771 A1* | 6/2009 | Buck | G16H 15/00 715/273 |
| 2009/0172773 A1 | 7/2009 | Moore | |
| 2009/0177477 A1 | 7/2009 | Nenov et al. | |
| 2009/0177492 A1 | 7/2009 | Hasan et al. | |
| 2009/0187407 A1 | 7/2009 | Soble et al. | |
| 2009/0198520 A1 | 8/2009 | Piovanetti-Perez | |
| 2009/0213123 A1 | 8/2009 | Crow | |
| 2009/0259136 A1* | 10/2009 | Schieb | A61B 5/374 600/544 |
| 2009/0270690 A1 | 10/2009 | Roos et al. | |
| 2010/0036676 A1 | 2/2010 | Safdi et al. | |
| 2010/0039296 A1 | 2/2010 | Marggraff et al. | |
| 2010/0076760 A1 | 3/2010 | Kraenzel et al. | |
| 2010/0076784 A1* | 3/2010 | Greenburg | G06Q 10/10 705/3 |
| 2010/0077289 A1 | 3/2010 | Das et al. | |
| 2010/0082657 A1 | 4/2010 | Paprizos et al. | |
| 2010/0088095 A1 | 4/2010 | John | |
| 2010/0094650 A1 | 4/2010 | Tran | |
| 2010/0094656 A1 | 4/2010 | Conant | |
| 2010/0094657 A1 | 4/2010 | Stern et al. | |
| 2010/0100376 A1 | 4/2010 | Harrington | |
| 2010/0131532 A1 | 5/2010 | Schultz | |
| 2010/0145736 A1 | 6/2010 | Rohwer | |
| 2010/0223216 A1 | 9/2010 | Eggert et al. | |
| 2010/0238323 A1 | 9/2010 | Englund | |
| 2010/0241662 A1 | 9/2010 | Keith, Jr. | |
| 2011/0015943 A1 | 1/2011 | Keldie et al. | |
| 2011/0035221 A1 | 2/2011 | Zhang et al. | |
| 2011/0063405 A1 | 3/2011 | Yam | |
| 2011/0063429 A1 | 3/2011 | Contolini et al. | |
| 2011/0066425 A1 | 3/2011 | Hudgins et al. | |
| 2011/0071675 A1 | 3/2011 | Wells et al. | |
| 2011/0096941 A1 | 4/2011 | Marzetta et al. | |
| 2011/0119163 A1* | 5/2011 | Smith | G06Q 40/12 705/30 |
| 2011/0145013 A1 | 6/2011 | McLaughlin | |
| 2011/0150420 A1 | 6/2011 | Cordonnier | |
| 2011/0153520 A1 | 6/2011 | Coifman | |
| 2011/0161113 A1* | 6/2011 | Rumak | G06Q 10/10 705/3 |
| 2011/0166884 A1 | 7/2011 | Lesselroth | |
| 2011/0178798 A1 | 7/2011 | Flaks et al. | |
| 2011/0178813 A1 | 7/2011 | Moore | |
| 2011/0202370 A1 | 8/2011 | Green, III et al. | |
| 2011/0238435 A1 | 9/2011 | Rapaport | |
| 2011/0246216 A1 | 10/2011 | Agrawal | |
| 2011/0251852 A1 | 10/2011 | Blas | |
| 2011/0286584 A1 | 11/2011 | Angel et al. | |
| 2011/0301982 A1 | 12/2011 | Green, Jr. et al. | |
| 2012/0020485 A1 | 1/2012 | Visser et al. | |
| 2012/0029918 A1 | 2/2012 | Bachtiger | |
| 2012/0053936 A1 | 3/2012 | Marvit | |
| 2012/0076316 A1 | 3/2012 | Zhu et al. | |
| 2012/0078626 A1 | 3/2012 | Tsai et al. | |
| 2012/0101847 A1 | 4/2012 | Johnson et al. | |
| 2012/0134507 A1 | 5/2012 | Dimitriadis et al. | |
| 2012/0155703 A1 | 6/2012 | Hernandez-Abrego et al. | |
| 2012/0158432 A1 | 6/2012 | Jain et al. | |
| 2012/0159391 A1 | 6/2012 | Berry et al. | |
| 2012/0173281 A1 | 7/2012 | DiLella et al. | |
| 2012/0197660 A1 | 8/2012 | Prodanovich | |
| 2012/0208166 A1 | 8/2012 | Ernst et al. | |
| 2012/0212337 A1 | 8/2012 | Montyne et al. | |
| 2012/0215551 A1 | 8/2012 | Flanagan et al. | |
| 2012/0215557 A1 | 8/2012 | Flanagan et al. | |
| 2012/0215559 A1 | 8/2012 | Flanagan et al. | |
| 2012/0239430 A1 | 9/2012 | Corfield | |
| 2012/0253801 A1 | 10/2012 | Santos-Lang et al. | |
| 2012/0253811 A1 | 10/2012 | Breslin | |
| 2012/0254917 A1 | 10/2012 | Burkitt et al. | |
| 2012/0323574 A1 | 12/2012 | Wang et al. | |
| 2012/0323575 A1 | 12/2012 | Gibbon et al. | |
| 2012/0323589 A1 | 12/2012 | Udani | |
| 2013/0017834 A1 | 1/2013 | Han et al. | |
| 2013/0035961 A1 | 2/2013 | Yegnanarayanan | |
| 2013/0041682 A1 | 2/2013 | Gottlieb et al. | |
| 2013/0041685 A1 | 2/2013 | Yegnanarayanan | |
| 2013/0064358 A1 | 3/2013 | Nusbaum | |
| 2013/0073306 A1 | 3/2013 | Shlain et al. | |
| 2013/0080879 A1* | 3/2013 | Darling | G06F 40/154 715/243 |
| 2013/0103400 A1 | 4/2013 | Yegnanarayanan et al. | |
| 2013/0138457 A1 | 5/2013 | Ragusa | |
| 2013/0173287 A1 | 7/2013 | Cashman et al. | |
| 2013/0188923 A1 | 7/2013 | Hartley et al. | |
| 2013/0238312 A1 | 9/2013 | Waibel | |
| 2013/0238329 A1 | 9/2013 | Casella dos Santos | |
| 2013/0238330 A1 | 9/2013 | Casella dos Santos | |
| 2013/0246098 A1 | 9/2013 | Habboush et al. | |
| 2013/0297347 A1 | 11/2013 | Cardoza et al. | |
| 2013/0297348 A1 | 11/2013 | Cardoza et al. | |
| 2013/0301837 A1 | 11/2013 | Kim et al. | |
| 2013/0311190 A1* | 11/2013 | Reiner | G10L 25/48 704/270 |
| 2013/0332004 A1 | 12/2013 | Gompert et al. | |
| 2013/0339030 A1 | 12/2013 | Ehsani et al. | |
| 2014/0019128 A1 | 1/2014 | Riskin et al. | |
| 2014/0035920 A1 | 2/2014 | Duwenhorst | |
| 2014/0050307 A1 | 2/2014 | Yuzefovich | |
| 2014/0073880 A1 | 3/2014 | Boucher | |
| 2014/0074454 A1 | 3/2014 | Brown | |
| 2014/0093135 A1 | 4/2014 | Reid et al. | |
| 2014/0096091 A1 | 4/2014 | Reid et al. | |
| 2014/0122109 A1 | 5/2014 | Ghanbari | |
| 2014/0142944 A1 | 5/2014 | Ziv et al. | |
| 2014/0169767 A1 | 6/2014 | Goldberg | |
| 2014/0188475 A1 | 7/2014 | Lev-Tov et al. | |
| 2014/0207491 A1 | 7/2014 | Zimmerman et al. | |
| 2014/0222526 A1 | 8/2014 | Shakil et al. | |
| 2014/0223467 A1 | 8/2014 | Hayton et al. | |
| 2014/0249818 A1 | 9/2014 | Yegnanarayanan et al. | |
| 2014/0249830 A1 | 9/2014 | Gallopyn et al. | |
| 2014/0249831 A1 | 9/2014 | Gallopyn et al. | |
| 2014/0249847 A1 | 9/2014 | Soon-Shiong et al. | |
| 2014/0278522 A1 | 9/2014 | Ramsey | |
| 2014/0278536 A1 | 9/2014 | Zhang et al. | |
| 2014/0279893 A1 | 9/2014 | Branton | |
| 2014/0281974 A1 | 9/2014 | Shi et al. | |
| 2014/0288968 A1 | 9/2014 | Johnson | |
| 2014/0306880 A1 | 10/2014 | Greif et al. | |
| 2014/0324477 A1 | 10/2014 | Oez | |
| 2014/0330586 A1 | 11/2014 | Riskin et al. | |
| 2014/0337016 A1 | 11/2014 | Herbig et al. | |
| 2014/0337048 A1 | 11/2014 | Brown et al. | |
| 2014/0343939 A1 | 11/2014 | Mathias et al. | |
| 2014/0362253 A1 | 12/2014 | Kim et al. | |
| 2014/0365239 A1 | 12/2014 | Sadeghi | |
| 2014/0365241 A1 | 12/2014 | Dillie et al. | |
| 2014/0365242 A1 | 12/2014 | Neff | |
| 2015/0046183 A1 | 2/2015 | Cireddu | |
| 2015/0046189 A1 | 2/2015 | Dao | |
| 2015/0052541 A1 | 2/2015 | Cheng | |
| 2015/0070507 A1 | 3/2015 | Kagan | |
| 2015/0086038 A1 | 3/2015 | Stein et al. | |
| 2015/0088514 A1 | 3/2015 | Typrin | |
| 2015/0088546 A1 | 3/2015 | Balram et al. | |
| 2015/0120305 A1 | 4/2015 | Buck et al. | |
| 2015/0120321 A1 | 4/2015 | David et al. | |
| 2015/0124277 A1 | 5/2015 | Ono et al. | |
| 2015/0124975 A1 | 5/2015 | Pontoppidan | |
| 2015/0172262 A1 | 6/2015 | Ortiz, Jr. et al. | |
| 2015/0172319 A1 | 6/2015 | Rodniansky | |
| 2015/0185312 A1 | 7/2015 | Gaubitch et al. | |
| 2015/0187209 A1 | 7/2015 | Brandt | |
| 2015/0248882 A1 | 9/2015 | Ganong, III et al. | |
| 2015/0278449 A1 | 10/2015 | Laborde | |

(56) References Cited

U.S. PATENT DOCUMENTS

| | | |
|---|---|---|
| 2015/0278534 A1 | 10/2015 | Thiyagarajan et al. |
| 2015/0290802 A1 | 10/2015 | Buehler et al. |
| 2015/0294079 A1 | 10/2015 | Bergougnan |
| 2015/0294089 A1 | 10/2015 | Nichols |
| 2015/0302156 A1 | 10/2015 | Parsadoust |
| 2015/0310174 A1 | 10/2015 | Coudert et al. |
| 2015/0310362 A1 | 10/2015 | Huffman |
| 2015/0356250 A1 | 12/2015 | Polimeni |
| 2015/0379200 A1 | 12/2015 | Gifford et al. |
| 2015/0379209 A1 | 12/2015 | Kusuma et al. |
| 2016/0012198 A1 | 1/2016 | Gainer, III et al. |
| 2016/0034643 A1 | 2/2016 | Zasowski |
| 2016/0063206 A1 | 3/2016 | Wilson |
| 2016/0064000 A1 | 3/2016 | Mizumoto et al. |
| 2016/0098521 A1 | 4/2016 | Koziol |
| 2016/0119338 A1 | 4/2016 | Cheyer |
| 2016/0148077 A1 | 5/2016 | Cox et al. |
| 2016/0163331 A1 | 6/2016 | Yamaguchi |
| 2016/0165350 A1 | 6/2016 | Benattar |
| 2016/0174903 A1* | 6/2016 | Cutaia ............... A61M 16/1005 600/301 |
| 2016/0176375 A1 | 6/2016 | Bolton et al. |
| 2016/0179770 A1 | 6/2016 | Koll et al. |
| 2016/0188809 A1 | 6/2016 | Legorburn |
| 2016/0191357 A1 | 6/2016 | Orner et al. |
| 2016/0196821 A1 | 7/2016 | Yegnanarayanan et al. |
| 2016/0203327 A1 | 7/2016 | Akkiraju et al. |
| 2016/0217807 A1 | 7/2016 | Gainsboro et al. |
| 2016/0234034 A1 | 8/2016 | Mahar et al. |
| 2016/0261930 A1 | 9/2016 | Kim |
| 2016/0275187 A1 | 9/2016 | Chowdhury et al. |
| 2016/0300020 A1 | 10/2016 | Wetta et al. |
| 2016/0342845 A1 | 11/2016 | Tien-Spalding et al. |
| 2016/0350950 A1 | 12/2016 | Ritchie et al. |
| 2016/0357538 A1 | 12/2016 | Lewallen et al. |
| 2016/0358632 A1 | 12/2016 | Lakhani et al. |
| 2016/0360336 A1 | 12/2016 | Gross et al. |
| 2016/0364606 A1 | 12/2016 | Conway et al. |
| 2017/0004260 A1 | 1/2017 | Moturu et al. |
| 2017/0011194 A1 | 1/2017 | Arshad et al. |
| 2017/0011740 A1 | 1/2017 | Gauci |
| 2017/0017834 A1 | 1/2017 | Sabitov et al. |
| 2017/0019744 A1 | 1/2017 | Matsumoto et al. |
| 2017/0046326 A1 | 2/2017 | Waibel |
| 2017/0069226 A1 | 3/2017 | Spinelli et al. |
| 2017/0076619 A1 | 3/2017 | Wallach et al. |
| 2017/0091246 A1 | 3/2017 | Risvik et al. |
| 2017/0093848 A1 | 3/2017 | Poisner et al. |
| 2017/0116384 A1 | 4/2017 | Ghani |
| 2017/0116392 A1 | 4/2017 | Casella dos Santos |
| 2017/0131384 A1 | 5/2017 | Davis et al. |
| 2017/0178664 A1 | 6/2017 | Wingate et al. |
| 2017/0197636 A1 | 7/2017 | Beauvais |
| 2017/0228500 A1 | 8/2017 | Massengale |
| 2017/0242840 A1 | 8/2017 | Lu et al. |
| 2017/0316775 A1 | 11/2017 | Le et al. |
| 2017/0334069 A1 | 11/2017 | Wang et al. |
| 2018/0004915 A1 | 1/2018 | Talbot et al. |
| 2018/0025093 A1 | 1/2018 | Xia et al. |
| 2018/0032702 A1 | 2/2018 | Casella dos Santos |
| 2018/0060282 A1* | 3/2018 | Kaljurand ............. G06F 40/103 |
| 2018/0075845 A1 | 3/2018 | Kochura |
| 2018/0081859 A1 | 3/2018 | Snider et al. |
| 2018/0107815 A1 | 4/2018 | Wu et al. |
| 2018/0122506 A1 | 5/2018 | Grantcharov et al. |
| 2018/0130554 A1 | 5/2018 | Cheng |
| 2018/0144120 A1 | 5/2018 | Fram |
| 2018/0144747 A1* | 5/2018 | Skarbovsky .......... G06F 40/232 |
| 2018/0156887 A1 | 6/2018 | Qiu et al. |
| 2018/0158461 A1 | 6/2018 | Wolff et al. |
| 2018/0158555 A1 | 6/2018 | Cashman et al. |
| 2018/0167243 A1 | 6/2018 | Gerdes |
| 2018/0181716 A1 | 6/2018 | Mander et al. |
| 2018/0197544 A1 | 7/2018 | Brooksby et al. |
| 2018/0197548 A1 | 7/2018 | Palakodety et al. |
| 2018/0218731 A1 | 8/2018 | Gustafson |
| 2018/0225277 A1 | 8/2018 | Alba |
| 2018/0232591 A1 | 8/2018 | Hicks et al. |
| 2018/0240538 A1 | 8/2018 | Koll et al. |
| 2018/0261307 A1 | 9/2018 | Couse et al. |
| 2018/0277017 A1 | 9/2018 | Cheung |
| 2018/0289291 A1 | 10/2018 | Richie |
| 2018/0310114 A1 | 10/2018 | Eronen et al. |
| 2018/0314689 A1 | 11/2018 | Wang et al. |
| 2018/0315428 A1 | 11/2018 | Johnson et al. |
| 2018/0336275 A1 | 11/2018 | Graham |
| 2019/0005959 A1 | 1/2019 | Cameron et al. |
| 2019/0012449 A1 | 1/2019 | Cheyer |
| 2019/0042606 A1 | 2/2019 | Griffith et al. |
| 2019/0051395 A1 | 2/2019 | Owen et al. |
| 2019/0096534 A1 | 3/2019 | Joao |
| 2019/0122766 A1 | 4/2019 | Strader et al. |
| 2019/0130073 A1 | 5/2019 | Sun et al. |
| 2019/0141031 A1 | 5/2019 | Devdas et al. |
| 2019/0172493 A1 | 6/2019 | Khan et al. |
| 2019/0182124 A1 | 6/2019 | Jeuk et al. |
| 2019/0214121 A1 | 7/2019 | O'Keeffe et al. |
| 2019/0246075 A1 | 8/2019 | Khadloya et al. |
| 2019/0251156 A1 | 8/2019 | Waibel |
| 2019/0265345 A1 | 8/2019 | Jungmaier et al. |
| 2019/0272844 A1 | 9/2019 | Sharma et al. |
| 2019/0313903 A1 | 10/2019 | McKinnon |
| 2020/0005939 A1 | 1/2020 | Stevens et al. |
| 2020/0005949 A1 | 1/2020 | Warkentine |
| 2020/0034753 A1 | 1/2020 | Hammad |
| 2020/0279107 A1 | 9/2020 | Staar et al. |
| 2021/0099433 A1 | 4/2021 | Soryal |

FOREIGN PATENT DOCUMENTS

| | | |
|---|---|---|
| EP | 1769771 A1 | 4/2007 |
| EP | 1927221 B1 | 11/2013 |
| JP | 2011182857 A | 9/2011 |
| JP | 2015533248 A | 11/2015 |
| KR | 20130118510 A | 10/2013 |
| WO | 0008585 A2 | 2/2000 |
| WO | 2013082087 A1 | 6/2013 |
| WO | 2014101472 A1 | 3/2014 |
| WO | 2014134089 A1 | 9/2014 |
| WO | 2016125053 A1 | 8/2016 |
| WO | 20160126813 A2 | 8/2016 |
| WO | 20160149794 A1 | 9/2016 |
| WO | 2017031972 A1 | 3/2017 |
| WO | 2017138934 A1 | 8/2017 |
| WO | 2019032778 A1 | 2/2019 |

OTHER PUBLICATIONS

Non-Final Office Action issued in related U.S. Appl. No. 16/192,358 dated Nov. 19, 2019.

Non-Final Office Action issued in related U.S. Appl. No. 16/059,944 dated Dec. 23, 2019.

Non-Final Office Action issued in related U.S. Appl. No. 16/059,818 dated Jan. 9, 2020.

Non-Final Office Action issued in related U.S. Appl. No. 16/058,912 dated Jan. 27, 2020.

Non-Final Office Action issued in related U.S. Appl. No. 16/292,920 dated Feb. 28, 2020.

Non-Final Office Action issued in related U.S. Appl. No. 16/100,030, dated Mar. 4, 2020.

Final Office Action issued in related U.S. Appl. No. 16/192,427, dated Mar. 6, 2020.

Notice of Allowance issued in related U.S. Appl. No. 16/271,616, dated Mar. 17, 2019.

Dibiase, J. H. et al., "Robust Localization in Reverberant Rooms," in Microphone Arrays—Signal Processing Techniques and Applications, Ch. 8, pp. 157-180.

Valin, Jean-Marc et al., "Robust Sound Source Localization Using a Microphone Array on a Mobile Robot," Proceedings of the 2003 IEEE/RSJ International Conference on Intelligent Robots and Systems, vol. 2, 2003, pp. 1228-1233.

(56) References Cited

OTHER PUBLICATIONS

Wang, L. et al., "Over-determined Source Separation and Localization Using Distributed Microphone," IEEE/ACM Transactions on Audio, Speech, and Language Processing, vol. 24, No. 9, Sep. 2016, pp. 1573-1588.
Notice of Allowance issued in related U.S. Appl. No. 16/108,959, dated Nov. 6, 2019.
Bahdanau, D. et al., "Neural Machine Translation by Jointly Learning to Align and Translate", Published as a Conference Paper at ICLR 2015, May 19, 2016, 15 pages.
Non-Final Office Action issued in related U.S. Appl. No. 16/059,818 dated Aug. 25, 2020.
Final Office Action issued in related U.S. Appl. No. 16/058,871, dated Mar. 19, 2020.
Final Office Action issued in related U.S. Appl. No. 16/059,944, dated Mar. 26, 2020.
Non-Final Office Action issued in related U.S. Appl. No. 16/058,936, dated Apr. 15, 2020.
Non-Final Office Action issued in related U.S. Appl. No. 16/058,941, dated Apr. 15, 2020.
Non-Final Office Action issued in related U.S. Appl. No. 16/059,895, dated Apr. 24, 2020.
Non-Final Office Action issued in related U.S. Appl. No. 16/059,974, dated Apr. 24, 2020.
Non-Final Office Action issued in related U.S. Appl. No. 16/059,986, dated Apr. 24, 2020.
Final Office Action issued in related U.S. Appl. No. 16/100,310, dated May 8, 2020.
Final Office Action issued in related U.S. Appl. No. 16/058,912 dated May 26, 2020.
Non-Final Office Action issued in related U.S. Appl. No. 16/271,616, dated May 29, 2020.
Final Office Action issued in related U.S. Appl. No. 16/192,358, dated Jun. 2, 2020.
Non-Final Office Action issued in related U.S. Appl. No. 16/292,895, dated Jun. 5, 2020.
Final Office Action issued in related U.S. Appl. No. 16/058,941 dated Jun. 23, 2020.
Final Office Action issued in related U.S. Appl. No. 16/058,936 dated Jun. 23, 2020.
Non-Final Office Action issued in related U.S. Appl. No. 16/058,856 dated Jul. 2, 2020.
Final Office Action issued in related U.S. Appl. No. 16/059,986 dated Jul. 6, 2020.
Final Office Action issued in related U.S. Appl. No. 16/059,974 dated Jul. 6, 2020.
Final Office Action issued in related U.S. Appl. No. 16/059,895 dated Jul. 6, 2020.
Non-Final Office Action issued in related U.S. Appl. No. 16/059,944 dated Jul. 13, 2020.
Notice of Allowance issued in related U.S. Appl. No. 16/271,616 dated Jul. 13, 2020.
Non-Final Office Action issued in related U.S. Appl. No. 16/058,826 dated Jul. 17, 2020.
Non-Final Office Action issued in related U.S. Appl. No. 16/058,914 dated Jul. 17, 2020.
Non-Final Office Action issued in related U.S. Appl. No. 16/058,925 dated Jul. 20, 2020.
Non-Final Office Action issued in related U.S. Appl. No. 16/058,894 dated Jul. 30, 2020.
Non-Final Office Action issued in related U.S. Appl. No. 16/292,877 dated Jul. 23, 2020.
Non-Final Office Action issued in related U.S. Appl. No. 16/058,883 dated Jul. 31, 2020.
Non-Final Office Action issued in related U.S. Appl. No. 16/058,829 dated Aug. 5, 2020.
Final Office Action issued in related U.S. Appl. No. 16/058,856 dated Aug. 12, 2020.
Final Office Action issued in related U.S. Appl. No. 16/292,920 dated Aug. 11, 2020.

Non-Final Office Action issued in related U.S. Appl. No. 16/058,912 dated Aug. 20, 2020.
Non-Final Office Action issued in related U.S. Appl. No. 16/100,030 dated Aug. 25, 2020.
Non-Final Office Action issued in U.S. Appl. No. 16/059,944 dated Sep. 28, 2018.
International Search Report and Written Opinion issued in counterpart International Application Serial No. PCT/US2018/045923 dated Oct. 2, 2018.
International Search Report and Written Opinion dated Oct. 3, 2018 in counterpart International Application Serial No. PCT/US2018/046024.
International Search Report and Written Opinion dated Oct. 3, 2018 in counterpart International Application Serial No. PCT/US2018/045982.
International Search Report and Written Opinion dated Oct. 3, 2018 in counterpart International Application Serial No. PCT/US2018/046008.
International Search Report and Written Opinion dated Oct. 2, 2018 in counterpart International Application Serial No. PCT/US2018/046034.
International Search Report and Written Opinion dated Oct. 3, 2018 in counterpart International Application Serial No. PC/US2018/045926.
International Search Report and Written Opinion dated Sep. 21, 2018 in counterpart International Application Serial No. PCT/US2018/046002.
Non-Final Office Action issued in U.S. Appl. No. 16/059,818 dated Nov. 2, 2018.
International Search Report and Written Opinion dated Oct. 24, 2018 in counterpart International Application Serial No. PCT/US2018/046041.
International Search Report and Written Opinion dated Oct. 16, 2018 in counterpart International Application Serial No. PCT/US2018/046029.
International Search Report and Written Opinion dated Oct. 11, 2018 in counterpart International Application Serial No. PCT/US2018/045994.
International Search Report and Written Opinion dated Oct. 22, 2018 in counterpart International Application Serial No. PCT/US2018/045903.
International Search Report and Written Opinion dated Oct. 22, 2018 in PCT Application Serial No. PCT/US2018/045917.
Jeffrey Klann et el., "An Intelligent Listening Framework for Capturing Encounter Notes from a Doctor-Patient Dialog", BMC Med Inform Decis Mak. 2009; 9(Suppl 1): S3, Published online Nov. 3, 2009. doi: 10.1186/1472-6947-9-S1-S3, 5 pages.
Non-Final Office Action issued in U.S. Appl. No. 16/058,871 dated Dec. 3, 2018.
International Search Report issued in PCT Application Serial No. PCT/US2018/045971 dated Oct. 30, 2018.
International Search Report issued in PCT Application Serial No. PCT/US2018/046049 dated Nov. 2, 2018.
International Search Report issued in PCT Application Serial No. PCT/US2018/045921 dated Oct. 16, 2018.
International Search Report issued in PCT Application Serial No. PCT/US2018/045896 dated Oct. 17, 2018.
Non-Final Office Action issued in U.S. Appl. No. 16/059,967 dated Jan. 2, 2019.
Non-Final Office Action issued in U.S. Appl. No. 16/058,951 dated Oct. 5, 2018.
A Study of Vision based Human Motion Recognition and Analysis to Kale et al., Dec. 2016.
International Search Report issued in PCT Application Serial No. PCT/US2018/045908 dated Oct. 19, 2018.
International Search Report issued in PCT Application Serial No. PCT/US2018/045936 dated Oct. 18, 2018.
International Search Report issued in PCT Application Serial No. PCT/US2018/045987 dated Oct. 12, 2018.
International Search Report issued in PCT Application Serial No. PCT/US2018/046006 dated Oct. 15, 2018.

(56) References Cited

OTHER PUBLICATIONS

Invitation to Pay Additional Fees and, Where Applicable, Protest Fee issued in PCT Application Serial No. PCT/US2012/072041 on Jun. 6, 2013.
International Search Report issued in PCT Application Serial No. PCT/US2012/072041 dated Aug. 2, 2013.
Alapetite et al., "Introducing vocal modality into electronics anaesthesia record systems: possible effects on work practices in the operating room", EACE '05 Proceedings of the 2005 Annual Conference on European Association of Cognitive Ergonomics, Jan. 1, 2005, 197-204.
Alapetite, "Speech recognition for the anaesthesia record during crisis scenarios", 2008, International Journal of Medical Informatics, 2008, 77(1), 448-460.
Cimiano et al., "Learning concept hierarchies from text with a guided hierarchical clustering algorithm", in C. Biemann and G. Paas (eds.), Proceedings of the ICML 2005 Workshop on Learning and Extending Lexical Ontologies with Machine Learning Methods, Bonn Germany, 2005.
Fan et al., "Prismatic: Inducing Knowledge from a Large Scale Lexicalized Relation Resource", Proceedings of the NAACL HLT 2010 First International Workshop on Formalisms and Methodology for Learning by Reading, pp. 122-127, Los Angeles, California, Jun. 2010.
Florian et al., "A Statistical Model for Multilingual Entity Detection and Tracking", Proceedings of the Human Language Technologies Conference 2004.
Gomez-Perez et al., "An overview of methods and tools for ontology learning from texts", Knowledge Engineering Review 19:3, pp. 187-212, 2004.
Grasso et al., "Automated Speech Recognition in Medical Applications", MD Computing, 1995, pp. 16-23.
Harris, "Building a Large-scale Commerical NLG System for an EMR", Proceedings of the Fifth International Natural Language Generation Conference, pp. 157-160, 2008.
Jungk et al., "A Case Study in Designing Speech Interaction with a Patient Monitor", J Clinical Monitoring and Computing, 2000, 295-307.
Klann et al., "An intelligent listening framework for capturing encounter notes from a doctor-patient dialog", BMC Medical Informatics and Decision Making 2009, published Nov. 3, 2009.
Meng et al., Generating Models of Surgical Procedures using UMLS Concepts and Multiple Sequence Alignment, AMIA Annual Symposium Proceedings, 2005, pp. 520-524.
MIT Computer Science and Artificial Intelligence Laboratory (CSAIL) Clinical Decision Making Group, "Fair Witness: Capturing Patient-Provider Encounter through Text, Speech, and Dialogue Processing", Last updated on Apr. 9, 2010, http://groups.csail.mit.edu/medg/projects/fw/.
Welty et al., "Large Scale Relation Detection", Proceedings of the NAACL HLT 2010 First International Workshop on Formalisms and Methodology for Learning by Reading, pp. 24-33, Jun. 2010.
Zafar et., "Continuous Speech Recognition for Clinicials", J Am Med Infor Assoc, 1999, pp. 195-204.
Final Office Action issued in U.S. Appl. No. 16/059,818 dated Feb. 28, 2019.
Non-Final Office Action issued in U.S. Appl. No. 16/100,030 dated Feb. 28, 2019.
Non-Final Office Action issued in U.S. Appl. No. 16/058,912 dated Mar. 6, 2019.
Final Office Action issued in U.S. Appl. No. 16/058,951 dated Apr. 4, 2019.
Final Office Action issued in U.S. Appl. No. 16/058,871 dated Apr. 8, 2019.
Non-Final Office Action issued in U.S. Appl. No. 16/059,944 dated Apr. 15, 2019.
International Search Report issued in PCT Application Serial No. PCT/US2019/020746 dated May 14, 2019.
Lenert et al., "Design and Evaluation of a Wireless Electronic Health Records System for Field Care in Mass Casualty Settings", Journal of the American Medical Informatics Association, Nov.-Dec. 2011; 18(6); pp. 842-852. <https://www.ncbi.nlm.nih.gov/pmc/articles/PMC3198000/>.
International Search Report issued in PCT Application Serial No. PCT/US2019/020742 dated May 14, 2019.
International Search Report issued in PCT Application Serial No. PCT/US2019/020739 dated May 17, 2019.
International Search Report issued in PCT Application Serial No. PCT/US2019/020763 dated May 23, 2019.
International Search Report issued in PCT Application Serial No. PCT/US2019/020765 dated May 23, 2019.
International Search Report issued in PCT Application Serial No. PCT/US2019/020778 dated May 23, 2019.
International Search Report issued in PCT Application Serial No. PCT/US2019/020771 dated May 30, 2019.
Non-Final Office Action issued in U.S. Appl. No. 16/059,818 dated Jun. 10, 2019.
International Search Report issued in PCT Application Serial No. PCT/US2019/020721 dated Jun. 6, 2019.
International Search Report issued in PCT Application Serial No. PCT/US2019/020755 dated Jun. 6, 2019.
Final Office Action issued in U.S. Appl. No. 16/059,967 dated Jul. 11, 2019.
Final Office Action issued in U.S. Appl. No. 16/100,030 dated Jul. 18, 2019.
Notice of Allowance issued in U.S. Appl. No. 16/100,030 dated Oct. 9, 2019.
Non-Final Office Action issued in U.S. Appl. No. 16/192,427 dated Oct. 3, 2019.
Non-Final Office Action issued in U.S. Appl. No. 16/058,951 dated Jul. 25, 2019.
International Search Report issued in International App. No. PCT/US2019/020788 dated Jul. 17, 2019.
Final Office Action issued in U.S. Appl. No. 16/058,912 dated Jul. 31, 2019.
Final Office Action issued in U.S. Appl. No. 16/059,944 dated Aug. 22, 2019.
Non-Final Office Action issued in U.S. Appl. No. 16/058,871 dated Sep. 23, 2019.
Final Office Action issued in U.S. Appl. No. 16/059,818 dated Sep. 25, 2019.
International Search Report and Written Opinion dated Nov. 15, 2019 in PCT Application Serial No. PCT/US2019/047689.
International Search Report and Written Opinion dated Jan. 11, 2021 in PCT Application Serial No. PCT/US2020/053504.
Non-Final Office Action issued in related U.S. Appl. No. 16/059,974, dated Dec. 18, 2020.
Notice of Allowance issued in related U.S. Appl. No. 16/058,912 dated Jan. 22, 2021.
Final Office Action issued in related U.S. Appl. No. 16/292,893 dated Jan. 28, 2021.
Notice of Allowance issued in related U.S. Appl. No. 16/100,030 dated Jan. 28, 2021.
Non-Final Office Action issued in related U.S. Appl. No. 16/441,777 dated Feb. 4, 2021.
Final Office Action issued in related U.S. Appl. No. 16/292,877 dated Feb. 8, 2021.
Non-Final Office Action issued in related U.S. Appl. No. 17/084,448 dated Feb. 10, 2021.
Non-Final Office Action issued in related U.S. Appl. No. 16/292,973 dated Feb. 12, 2021.
Final Office Action issued in related U.S. Appl. No. 16/192,427 dated Feb. 22, 2021.
Final Office Action issued in related U.S. Appl. No. 16/293,032 dated Mar. 1, 2021.
Non-Final Office Action issued in related U.S. Appl. No. 16/270,888 dated Mar. 2, 2021.
Notice of Allowance issued in related U.S. Appl. No. 16/058,856 dated Mar. 9, 2021.
Final Office Action issued in related U.S. Appl. No. 16/058,871, dated Mar. 18, 2021.
"Zhou et al., ""Applying the Narve Bayes Classifier to Assist Users in Detecting Speech Recognition Errors,"" Proceedings of the 38th

(56) References Cited

OTHER PUBLICATIONS

Annual Hawaii International Conference on System Sciences, Big Island, HI, USA, 2005, pp. 183b-183b, doi: 10.1109/HICSS.2005.99."

Abdulkader et al., "Low Cost Correction of OCR Errors Using Learning in a Multi-Engine Environment," 2009 10th International Conference on Document Analysis and Recognition, Barcelona, 2009, pp. 576-580, doi: 10.1109/ICDAR.2009.242.

Final Office Action issued in related U.S. Appl. No. 16/059,895 dated Mar. 24, 2021.

Final Office Action issued in related U.S. Appl. No. 16/059,974 dated Mar. 24, 2021.

Final Office Action issued in related U.S. Appl. No. 16/059,986 dated Mar. 24, 2021.

Non-Final Office Action issued in related U.S. Appl. No. 16/292,895 dated Mar. 25, 2021.

Non-Final Office Action issued in related U.S. Appl. No. 16/292,920 dated Mar. 26, 2021.

Non-Final Office Action issued in related U.S. Appl. No. 16/270,888 dated Mar. 26, 2021.

Non-Final Office Action issued in related U.S. Appl. No. 16/271,329 dated Mar. 26, 2021.

Hu et al., "Deep Multimodel Speaker Naming", Computing Research Repository, vol. abs/1507.04831, 2015 (Year: 2015).

Final Office Action issued in related U.S. Appl. No. 16/271,029 dated Apr. 1, 2021.

Non-Final Office Action issued in related U.S. Appl. No. 16/058,826 dated April 6. 2021.

Notice of Allowance issued in related U.S. Appl. No. 16/058,871 dated Apr. 9, 2021.

Final Office Action issued in related U.S. Appl. No. 17/084,310 dated Apr. 12, 2021.

Non-Final Office Action issued in related U.S. Appl. No. 16/441,740 dated Apr. 14, 2021.

Non-Final Office Action issued in related U.S. Appl. No. 16/442,247 dated Apr. 15, 2021.

Non-Final Office Action issued in related U.S. Appl. No. 16/058,925 dated Apr. 16, 2021.

Non-Final Office Action issued in related U.S. Appl. No. 16/058,914 dated Apr. 16, 2021.

Non-Final Office Action issued in related U.S. Appl. No. 16/058,894 dated Apr. 16, 2021.

International Search Report and Written Opinion dated Aug. 31, 2020 in related PCT Application Serial No. PCT/US2020/037226.

Non-Final Office Action issued in related U.S. Appl. No. 16/192,358, dated Nov. 27, 2020.

Final Office Action issued in related U.S. Appl. No. 16/058,803, dated Nov. 30, 2020.

Final Office Action issued in reiated U.S. Appl. No. 16/058,925, dated Nov. 30, 2020.

Final Office Action issued in related U.S. Appl. No. 16/058,914, dated Nov. 30, 2020.

Final Office Action issued in related U.S. Appl. No. 16/292,895, dated Nov. 30, 2020.

Final Office Action issued in related U.S. Appl. No. 16/058,826, dated Nov. 30, 2020.

Final Office Action issued in related U.S. Appl. No. 16/058,883, dated Nov. 30, 2020.

Final Office Action issued in related U.S. Appl. No. 16/058,894 dated Dec. 1, 2020.

Final Office Action issued in related U.S. Appl. No. 16/059,818, dated Dec. 4, 2020.

Non-Final Office Action issued in related U.S. Appl. No. 16/059,895, dated Dec. 9, 2020.

Non-Final Office Action issued in related U.S. Appl. No. 16/059,986, dated Dec. 18, 2020.

Non-Final Office Action issued in related U.S. Appl. No. 17/084,310, dated Dec. 21, 2020.

Final Office Action issued in related U.S. Appl. No. 16/058,941 dated Dec. 22, 2020.

Final Office Action issued in related U.S. Appl. No. 16/058,936, dated Dec. 22, 2020.

Final Office Action issued in related U.S. Appl. No. 16/059,944, dated Dec. 28, 2020.

Final Office Action issued in related U.S. Appl. No. 16/058,829, dated Jan. 11, 2021.

Angles, R., "A Comparison of Current Graph Database Models", In: 2012 IEEE 28th International Conference on Data Engineering Workshops, Apr. 5, 2012 (Apr. 5, 2012) Retrieved on Aug. 5, 2020 (Aug. 5, 2020) from URL:https://ieeexplore.ieee.org/document/6313676 entire document, 7 pages.

Notice of Allowance issued in related U.S. Appl. No. 16/100,030 dated Jan. 11, 2021.

Notice of Allowance issued in related U.S. Appl. No. 16/058,856 dated Jan. 19. 2021.

International Search Report and Written Opinion dated Aug. 19, 2020 in PCT Application Serial No. PCT/US2020/037284.

Non-Final Office Action issued in related U.S. Appl. No. 16/058,803 dated Sep. 3, 2020.

YouTube video clip entitled "Nuance PowerMic Mobile gives clinicians greater mobility", retrieved from Internet: https://www.youtube.com/watch?v=OjqiePRFti@feature=emb-logo (Year: 2015), 3 pages.

Non-Final Office Action issued in related U.S. Appl. No. 16/271,029 dated Sep. 8, 2020.

Non-Final Office Action issued in related U.S. Appl. No. 16/293,032 dated Sep. 16, 2020.

Non-Final Office Action issued in related U.S. Appl. No. 16/192,427 dated Sep. 21, 2020.

Non-Final Office Action issued in related U.S. Appl. No. 16/292,893 dated Oct. 2, 2020.

David, G. C. et al., "Listening to what is said—transcribing what is heard: the impact of speech recognition technology (SRT) on the practice of medical transcription (MT)", Sociology of Heath and Illness, vol. 31, No. 6, pp. 924-938, (2009).

Non-Final Office Action issued in related U.S. Appl. No. 16/058,871 dated Oct. 5, 2020.

Non-Final Office Action issued in related U.S. Appl. No. 16/058,941 dated Oct. 26, 2020.

Non-Final Office Action issued in related U.S. Appl. No. 16/058,936 dated Oct. 26, 2020.

Notice of Allowance issued in related U.S. Appl. No. 17/084,310 dated Jul. 7, 2021.

Notice of Allowance issued in related U.S. Appl. No. 17/084,310 dated Jul. 9, 2021.

Notice of Allowance issued in related U.S. Appl. No. 16/058,941 dated Jul. 14, 2021.

Notice of Allowance issued in related U.S. Appl. No. 16/292,920 dated Jul. 15, 2021.

Supplementary European Search Report issued in counterpart Application Serial No. 188344752.8 dated Mar. 3, 2021.

Non-Final Office Action issued in related U.S. Appl. No. 16/058,883 dated Apr. 28, 2021.

Notice of Allowance issued in related U.S. Appl. No. 16/059,944 dated Apr. 30, 2021.

Notice of Allowance issued in related U.S. Appl. No. 17/084,448 dated May 14, 2021.

Final Office Action issued in related U.S. Appl. No. 17/084,448 dated Jun. 1, 2021.

Non-Final Office Action issued in related U.S. Appl. No. 16/292,893 dated Jun. 9, 2021.

David, G. C., Garcia, A. C., Rawls, A. W., & Chand, D. (2009). Listening to what is said—transcribing what is heard: the impact of speech recognition technology (SRT) on the practice of medical transcription (MT). Sociology of Health & Illness, 31 (6), 924-938. (Year: 2009).

Notice of Allowance issued in related U.S. Appl. No. 16/293,032 dated Jun. 14, 2021.

Non-Final Office Action issued in related U.S. Appl. No. 16/293,032 dated Jun. 24, 2021.

Non-Final Office Action issued in related U.S. Appl. No. 16/058,803 dated Jun. 24, 2021.

(56) References Cited

OTHER PUBLICATIONS

Non-Final Office Action issued in related U.S. Appl. No. 16/058,829 dated Jun. 25, 2021.
Final Office Action issued in related U.S. Appl. No. 16/059,818 dated Jun. 25, 2021.
Notice of Allowance issued in related U.S. Appl. No. 16/059,818 dated Jul. 2, 2021.
Non-Final Office Action issued in related U.S. Appl. No. 16/773,447 dated Jul. 20, 2021.
Notice of Allowance issued in related U.S. Appl. No. 16/442,247 dated Jul. 22, 2021.
Communication issuing supplementary European Search Report of May 14, 2021 and Extended European Search Report dated Apr. 16, 2021 in counterpart Application Serial No. EP 18844226.3.
Communication issuing supplementary European Search Report of Apr. 8, 2021 and Extended European Search Report dated Mar. 10, 2021 in counterpart Application Serial No. EP 18845046.4.
YouTube video clip entitled "Nuance PowerMic Mobile gives clinicians greater mobility", retrieved from Internet: https://www.youtube.com/watch?v=OjqiePRFtl@feature=emb-logo (Year: 2015), 3 pages.
Gross R, et al: "Towards a multimodal meeting record", Multimedia and Expo, 2000. ICME 2000. 2000 IEEE International Conference in New York, NY, USA Jul. -Aug. 2, 2000, Piscataway, NJ, USA, IEEE, US, vol. 3, Jul. 30, 2000 (Jul. 30, 2000_, pp. 1593-1596, XP010512812, DOI: 10.1109/ICME.2000.871074 ISBN: 978-0-7803-6536-0 *the whole document*.
Communication issuing supplementary European Search Report of Apr. 8, 2021 and Extended European Search Report dated Mar. 10, 2021 counterpart Application Serial No. EP 18842996.3.
Communication issuing supplementary European Search Report of May 19, 2021 and Extended European Search Report dated Apr. 19, 2021 in counterpart Application Serial No. EP 18844530.8.
Communication issuing supplementary European Search Report of May 19, 2021 and Extended Europe Search Report dated Apr. 19, 2021 in counterpart Application Serial No. EP 18843844.1.
Nadir, Weibel, et al.: "Lab-in-a-Box: semi-automatic tracking of activity in the medical office", Personal and Ubiqitous Computing, Springer Verlag, Lond, GB, vol. 19, No. 2, Sep. 28, 2014 (Sep. 28, 2014) pp. 317-334, XP058066121, ISSN: 1617-4909, DOI: 10.1007/S00779-014-0821-0 *abstract* *Section 4, The Lab-in-a-Box; p. 321-p. 327* *Section 5.2, "Data collection and analysis"; p. 330-p. 331* *table 1* *figures 7,8*.
Communication issuing supplementary European Search Report of May 28, 2021 and Extended European Search Report dated May 3, 2021 in counterpart Application Serial No. EP 18843648.9.
Communication issuing supplementary European Search Report of May 28, 2021 and Extended European Search Report dated Apr. 16, 2021 in counterpart Application Serial No. EP 18843945.9.
Communication issuing supplementary European Search Report of May 19, 2021 and Extended European Search Report dated Apr. 19, 2021 in counterpart Application Serial No. EP 18844669.4.
Yang, et al., "The Design and Implementation of a Smart e-Receptionist", IEE Potentials, IEEE, New York, NY, US, vo. 32, No. 4, Jul. 22, 2013 (Jul. 22, 2013), pp. 22-27, XP011522905, ISSN: 0278-6648, DOI: 10.1109/MPOT.2012.2213851 *the whole document*.
Communication issuing supplementary European Search Report of May 14, 2021 and Extended European Search Report dated Apr. 16, 2021 in counterpart Application Serial No. EP 18843175.3.
Communication issuing supplementary European Search Report of May 28, 2021 and Extended European Search Report dated Apr. 29, 2021 in counterpart Application Serial No. EP 18845144.7.
Non-Final Office Action dated Aug. 6, 2021 in counterpart U.S. Appl. No. 16/270,782.
Final Office Action dated Aug. 19, 2021 in counterpart U.S. Appl. No. 16/292,973.
Communication issuing supplementary European Search Report of Apr. 12, 2021 and Extended European Search Report of Mar. 12, 2021 in counterpart Application Serial No. EP 18843255.3.
Communication issuing supplementary European Search Report of May 26, 2021 and Extended European Search Report of Apr. 30, 2021 in counterpart Application Serial No. EP 18844675.1.
Communication issuing supplementary European Search Report of Mar. 30, 2021 and Extended European Search Report of Mar. 3, 2021 in counterpart Application Serial No. EP 18844752.8.
Shivappa, S. et al., "Role of Head Pse Estimation in Speech Acquisition from Distant Microphones," Acoustics, Speech and Signal Processing, ICASSP 2009, IEEE International Conference on IEEE, pp. 3557-3560, Apr. 19, 2009.
Communication issuing supplementary European Search Report of Apr. 6, 2021 and Extended European Search Report dated Mar. 8, 2021 in counterpart Application Serial No. EP 18844407.9.
Communication issuing supplementary European Search Report of Apr. 12, 2021 and Extended European Search Report of Apr. 19, 2021 in counterpart Application Serial No. EP 18843873.3.
Communication issuing supplementary European Search Report of Apr. 12, 2021 and Extended European Search Report of Mar. 11, 2021 in counterpart Application Serial No. EP 18843329.6.
Communication issuing supplementary European Search Report of Apr. 13, 2021 and Extended European Search Report of Apr. 19, 2021 in counterpart Application Serial No. EP 18843586.1.
Communication issuing supplementary European Search Report of Apr. 16, 2021 and Extended European Search Report of Mar. 22, 2021 in counterpart Application Serial No. EP 18843254.6.
Communication issuing supplementary European Search Report of May 26, 2021 and Extended European Search Report of Apr. 30, 2021 in counterpart Application Serial No. EP 18844406.1.
Non-Final Office Action issued in counterpart U.S. Appl. No. 16/271,029 dated Sep. 15, 2021.
Notice of Allowance issued in counterpart U.S. Appl. No. 16/059,895 dated Sep. 13, 2021.
Final Office Action issued in counterpart U.S. Appl. No. 16/270,888 dated Sep. 9, 2021.
Notice of Allowance issued in counterpart U.S. Appl. No. 17/084,448 dated Sep. 22, 2021.
Non-Final Office Action issued in counterpart U.S. Appl. No. 16/059,967 dated Sep. 20, 2021.
Klaan et al. , "An Intelligent listening framework for capturing encounter notes from a doctor-patient dialog," BMC Medical Informatics and Decision Making, vol. 9, Suppl , Suppl 1, S3. Nov. 2009.
Final Office Action issued in counterpart U.S. Appl. No. 16/292,895 dated Sep. 30, 2021.
Notice of Allowance issued in counterpart U.S. Appl. No. 16/059,974 dated Oct. 5, 2021.
Notice of Allowance issued in counterpart U.S. Appl. No. 16/059,986 dated Oct. 12, 2021.
Final Office Action issued in counterpart U.S. Appl. No. 16/058,826 dated Oct. 21, 2021.
Final Office Action issued in counterpart U.S. Appl. No. 16/058,894 dated Oct. 29, 2021.
Final Office Action issued in counterpart U.S. Appl. No. 16/058,883 dated Oct. 29, 2021.
Final Office Action issued in counterpart U.S. Appl. No. 16/058,925 dated Oct. 29, 2021.
Final Office Action issued in counterpart U.S. Appl. No. 16/058,914 dated Oct. 29, 2021.
Unknown, You Tube video clip entitled "Nuance Healthcare Florence Workflow Concept with Samsung Samrtwatch Demo English," retrieved from Internet: https://www.youtube.com/watch?v=I-NVD60oyn) (Year: 2015).
Final Office Action issued in counterpart U.S. Appl. No. 16/292,893 dated Nov. 15, 2021.
Notice of Allowance issued counterpart U.S. Appl. No. 16/292,920 dated Nov. 10, 2021.
Notice of Allowance issued in counterpart U.S. Appl. No. 17/084,310 dated Nov. 12, 2021.
Notice of Allowance issued in counterpart U.S. Appl. No. 16/442,247 dated Nov. 15, 2021.
Notice of Allowance issued in counterpart U.S. Appl. No. 16/441,740 dated Nov. 15, 2021.

(56) References Cited

OTHER PUBLICATIONS

Luck, J. et al., Using standardized patients to measure physicians' practice: validation study using audio recordings. Bmj, 325(7366), 679 (2002).
Final Office Action issued in related U.S. Appl. No. 16/293,032 dated Nov. 19, 2021.
Non-Final Office Action issued in related U.S. Appl. No. 17/210,052 dated Nov. 19, 2021.
Notice of Allowance issued in related U.S. Appl. No. 16/192,427 dated Dec. 3, 2021.
Notice of Allowance issued in U.S. Appl. No. 16/192,427 on Dec. 8, 2021.
Notice of Allowance issued in U.S. Appl. No. 16/271,329 datec Dec. 13, 2021.
Notice of Allowance issued in U.S. Appl. No. 16/773,447 dated Dec. 15, 2021.
Notice of Allowance issued in U.S. Appl. No. 16/059,986 dated Dec. 15, 2021.
Non-Final Office Action issued in U.S. Appl. No. 16/588,475 dated Jan. 10, 2022.
Notice of Allowance issued in U.S. Appl. No. 16/059,895 dated Jan. 18, 2022.
Non-Final Office Action issued in U.S. Appl. No. 16/270,888 dated Jan. 20, 2022.
International Search Report and Written Opinion dated Dec. 1, 2021 in PCT Application Serial No. PCT/US2021/056265.

\* cited by examiner

Runtime example
500

| Stage | Concepts marked up | Concepts formatted | Example |
|---|---|---|---|
| ASR output | No | No | Patient: so then I checked my temperature and it was a hundred and one |
| Seq-2-Seq output | Yes | No | ...he developed a temperature to <temperature> a hundred and one </temperature> orally... |
| Report text | Yes | Yes | ...he developed a temperature to 101°F orally... |

FIG. 5

Alignment Concept example

| Stage | Example | Concepts marked up | Concepts formatted |
|---|---|---|---|
| ASR output lattice | Patient so then I checked my temperature and it was a hundred and one | No | No |
| Report text | A temperature to 101°F orally | No | Yes |
| Report text marked up using text-concept grammar | A temperature to <temperature> a hundred and one </temperature> orally | Yes | No |
| Marked up report text augmented via concept verbalization grammar | a temperature of <temperature> ((one oh one \| a hundred and one \| one hundred one \| ...) [Fahrenheit] \| thirty eight [Celsius] ) </temperature> | Yes | No |
| Ambiguity-resolved marked up report text via ASR output alignment | A temperature to <temperature> a hundred and one </temperature> orally | Yes | No |

FIG. 7

SYSTEM AND METHOD FOR CONCEPT FORMATTING

RELATED CASES

This application claims the benefit of U.S. Provisional Application No. 62/638,809 filed on 5 Mar. 2018, the contents of which are all incorporated herein by reference.

BACKGROUND

Automated Clinical Documentation (ACD) may be used, e.g., to turn transcribed conversational (e.g., physician-patient) speech into formatted (e.g., medical) reports. In some implementations, the "heart" of the process may be sequence-to-sequence ("seq2seq") models, which transform the ASR output to a final report. In current systems, different examples of various concepts (such as dates, vital signs and dosage) are "rendered" by the seq2seq model. That is, the model must typically learn the way the concepts are formatted.

BRIEF SUMMARY OF DISCLOSURE

In one example implementation, a method, performed by one or more computing devices, may include but is not limited to mapping, by a computing device, an automatic speech recognition output of a conversation to a concept marker and a verbalized version of a value associated with the concept marker based upon, at least in part, the automatic speech recognition output of the conversation. The concept marker and the verbalized version of the value associated with the concept marker may be replaced with a formatted version. A plurality of user selectable format configurations of the formatted version may be provided as a textual output in a user interface.

One or more of the following example features may be included. A concept identification grammar may be applied to the textual output of the medical report. The verbalized version may be selected from a plurality of paths provided by a concept verbalization grammar. A path of the plurality of paths may be selected based upon, at least in part, an edit distance alignment between the automatic speech recognition output and an associated target graph. A user selected format configuration of the plurality of user selectable format configurations selected by a user may be received. A model may be trained using concept verbalization disambiguation. The model may be a sequence-to-sequence model.

In another example implementation, a computing system may include one or more processors and one or more memories configured to perform operations that may include but are not limited to an automatic speech recognition output of a conversation to a concept marker and a verbalized version of a value associated with the concept marker based upon, at least in part, the automatic speech recognition output of the conversation. The concept marker and the verbalized version of the value associated with the concept marker may be replaced with a formatted version. A plurality of user selectable format configurations of the formatted version may be provided as a textual output in a user interface.

One or more of the following example features may be included. A concept identification grammar may be applied to the textual output of the medical report. The verbalized version may be selected from a plurality of paths provided by a concept verbalization grammar. A path of the plurality of paths may be selected based upon, at least in part, an edit distance alignment between the automatic speech recognition output and an associated target graph. A user selected format configuration of the plurality of user selectable format configurations selected by a user may be received. A model may be trained using concept verbalization disambiguation. The model may be a sequence-to-sequence model.

In another example implementation, a computer program product may reside on a computer readable storage medium having a plurality of instructions stored thereon which, when executed across one or more processors, may cause at least a portion of the one or more processors to perform operations that may include but are not limited to an automatic speech recognition output of a conversation to a concept marker and a verbalized version of a value associated with the concept marker based upon, at least in part, the automatic speech recognition output of the conversation. The concept marker and the verbalized version of the value associated with the concept marker may be replaced with a formatted version. A plurality of user selectable format configurations of the formatted version may be provided as a textual output in a user interface.

One or more of the following example features may be included. A concept identification grammar may be applied to the textual output of the medical report. The verbalized version may be selected from a plurality of paths provided by a concept verbalization grammar. A path of the plurality of paths may be selected based upon, at least in part, an edit distance alignment between the automatic speech recognition output and an associated target graph. A user selected format configuration of the plurality of user selectable format configurations selected by a user may be received. A model may be trained using concept verbalization disambiguation. The model may be a sequence-to-sequence model.

The details of one or more example implementations are set forth in the accompanying drawings and the description below. Other possible example features and/or possible example advantages will become apparent from the description, the drawings, and the claims. Some implementations may not have those possible example features and/or possible example advantages, and such possible example features and/or possible example advantages may not necessarily be required of some implementations.

BRIEF DESCRIPTION OF THE DRAWINGS

FIG. 5 is an example runtime diagram of a formatting process according to one or more example implementations of the disclosure;

FIG. 7 is an example alignment concept diagram of a formatting process according to one or more example implementations of the disclosure;

Like reference symbols in the various drawings indicate like elements.

DETAILED DESCRIPTION

Figure 1:
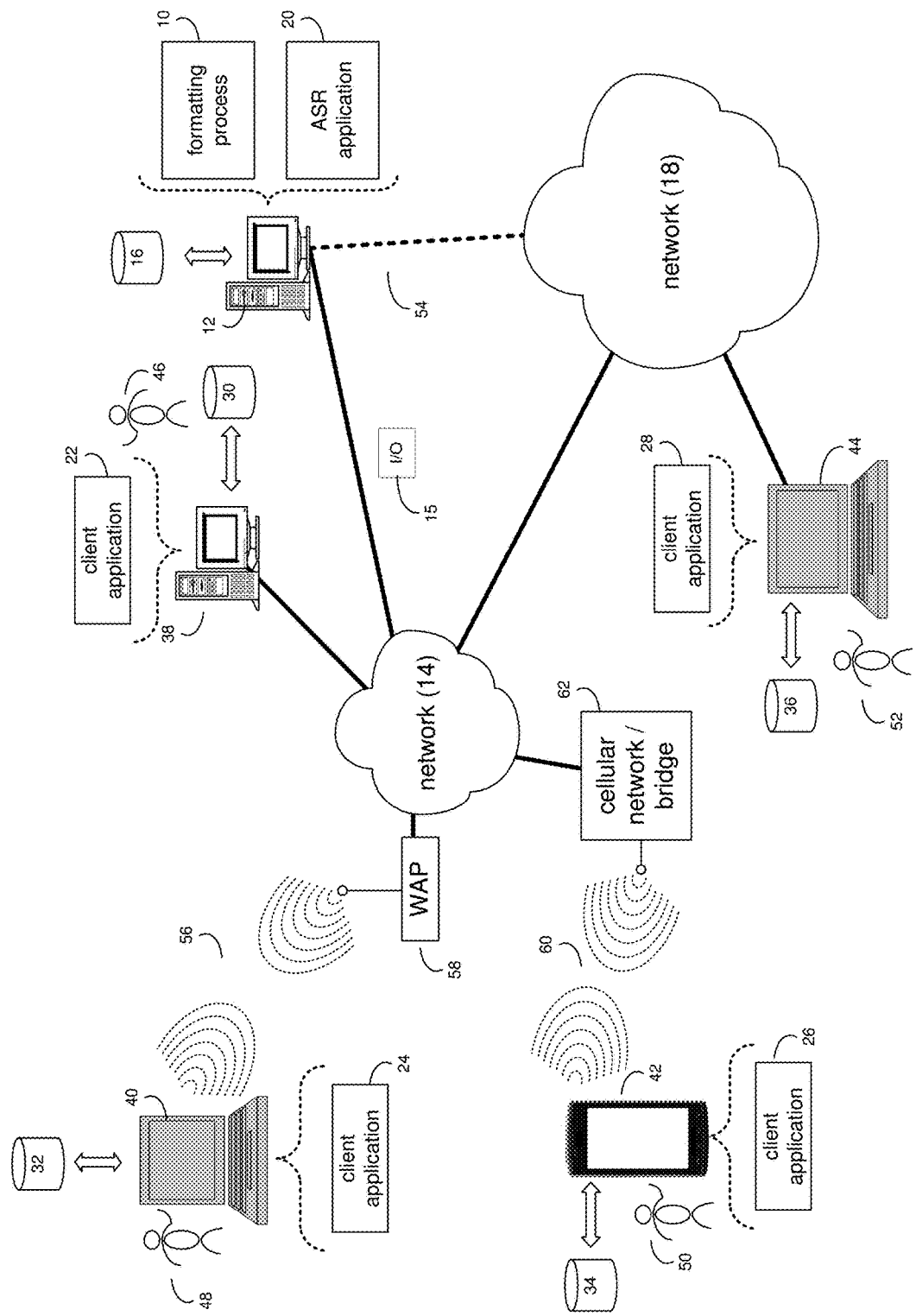
FIG. 1 is an example diagrammatic view of a formatting process coupled to an example distributed computing network according to one or more example implementations of the disclosure.

System Overview:

In some implementations, the present disclosure may be embodied as a method, system, or computer program product. Accordingly, in some implementations, the present disclosure may take the form of an entirely hardware implementation, an entirely software implementation (including firmware, resident software, micro-code, etc.) or an implementation combining software and hardware aspects that may all generally be referred to herein as a "circuit," "module" or "system." Furthermore, in some implementations, the present disclosure may take the form of a computer program product on a computer-usable storage medium having computer-usable program code embodied in the medium.

In some implementations, any suitable computer usable or computer readable medium (or media) may be utilized. The computer readable medium may be a computer readable signal medium or a computer readable storage medium. The computer-usable, or computer-readable, storage medium (including a storage device associated with a computing device or client electronic device) may be, for example, but is not limited to, an electronic, magnetic, optical, electromagnetic, infrared, or semiconductor system, apparatus, device, or any suitable combination of the foregoing. More specific examples (a non-exhaustive list) of the computer-readable medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a digital versatile disk (DVD), a static random access memory (SRAM), a memory stick, a floppy disk, a mechanically encoded device such as punch-cards or raised structures in a groove having instructions recorded thereon, a media such as those supporting the internet or an intranet, or a magnetic storage device. Note that the computer-usable or computer-readable medium could even be a suitable medium upon which the program is stored, scanned, compiled, interpreted, or otherwise processed in a suitable manner, if necessary, and then stored in a computer memory. In the context of the present disclosure, a computer-usable or computer-readable, storage medium may be any tangible medium that can contain or store a program for use by or in connection with the instruction execution system, apparatus, or device.

In some implementations, a computer readable signal medium may include a propagated data signal with computer readable program code embodied therein, for example, in baseband or as part of a carrier wave. In some implementations, such a propagated signal may take any of a variety of forms, including, but not limited to, electromagnetic, optical, or any suitable combination thereof. In some implementations, the computer readable program code may be transmitted using any appropriate medium, including but not limited to, the internet, wireline, optical fiber cable, RF, etc. In some implementations, a computer readable signal medium may be any computer readable medium that is not a computer readable storage medium and that can communicate, propagate, or transport a program for use by or in connection with an instruction execution system, apparatus, or device.

In some implementations, computer program code for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java®, Smalltalk, C++ or the like. Java® and all Java-based trademarks and logos are trademarks or registered trademarks of Oracle and/or its affiliates. However, the computer program code for carrying out operations of the present disclosure may also be written in conventional procedural programming languages, such as the "C" programming language, PASCAL, or similar programming languages, as well as in scripting languages such as Javascript, PERL, or Python. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network (LAN) or a wide area network (WAN), or the connection may be made to an external computer (for example, through the internet using an Internet Service Provider). In some implementations, electronic circuitry including, for example, programmable logic circuitry, field-programmable gate arrays (FPGAs) or other hardware accelerators, micro-controller units (MCUs), or programmable logic arrays (PLAs) may execute the computer readable program instructions/code by utilizing state information of the computer readable program instructions to personalize the electronic circuitry, in order to perform aspects of the present disclosure.

In some implementations, the flowchart and block diagrams in the figures illustrate the architecture, functionality, and operation of possible implementations of apparatus (systems), methods and computer program products according to various implementations of the present disclosure. Each block in the flowchart and/or block diagrams, and combinations of blocks in the flowchart and/or block diagrams, may represent a module, segment, or portion of code, which comprises one or more executable computer program instructions for implementing the specified logical function(s)/act(s). These computer program instructions may be provided to a processor of a general purpose computer, special purpose computer, or other programmable data processing apparatus to produce a machine, such that the computer program instructions, which may execute via the processor of the computer or other programmable data processing apparatus, create the ability to implement one or more of the functions/acts specified in the flowchart and/or block diagram block or blocks or combinations thereof. It should be noted that, in some implementations, the functions noted in the block(s) may occur out of the order noted in the figures (or combined or omitted). For example, two blocks shown in succession may, in fact, be executed substantially concurrently, or the blocks may sometimes be executed in the reverse order, depending upon the functionality involved.

In some implementations, these computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks or combinations thereof.

In some implementations, the computer program instructions may also be loaded onto a computer or other programmable data processing apparatus to cause a series of operational steps to be performed (not necessarily in a particular order) on the computer or other programmable apparatus to produce a computer implemented process such that the instructions which execute on the computer or other programmable apparatus provide steps for implementing the functions/acts (not necessarily in a particular order) specified in the flowchart and/or block diagram block or blocks or combinations thereof.

Referring now to the example implementation of FIG. 1, there is shown formatting process 10 that may reside on and may be executed by a computer (e.g., computer 12), which may be connected to a network (e.g., network 14) (e.g., the internet or a local area network). Examples of computer 12 (and/or one or more of the client electronic devices noted below) may include, but are not limited to, a storage system (e.g., a Network Attached Storage (NAS) system, a Storage Area Network (SAN)), a personal computer(s), a laptop computer(s), mobile computing device(s), a server computer, a series of server computers, a mainframe computer (s), or a computing cloud(s). As is known in the art, a SAN may include one or more of the client electronic devices, including a RAID device and a NAS system. In some implementations, each of the aforementioned may be generally described as a computing device. In certain implementations, a computing device may be a physical or virtual device. In many implementations, a computing device may be any device capable of performing operations, such as a dedicated processor, a portion of a processor, a virtual processor, a portion of a virtual processor, portion of a virtual device, or a virtual device. In some implementations, a processor may be a physical processor or a virtual processor. In some implementations, a virtual processor may correspond to one or more parts of one or more physical processors. In some implementations, the instructions/logic may be distributed and executed across one or more processors, virtual or physical, to execute the instructions/logic. Computer 12 may execute an operating system, for example, but not limited to, Microsoft® Windows®; Mac® OS X®; Red Hat® Linux®, Windows® Mobile, Chrome OS, Blackberry OS, Fire OS, or a custom operating system. (Microsoft and Windows are registered trademarks of Microsoft Corporation in the United States, other countries or both; Mac and OS X are registered trademarks of Apple Inc. in the United States, other countries or both; Red Hat is a registered trademark of Red Hat Corporation in the United States, other countries or both; and Linux is a registered trademark of Linus Torvalds in the United States, other countries or both).

In some implementations, as will be discussed below in greater detail, a formatting process, such as formatting process 10 of FIG. 1, may map, by a computing device, an automatic speech recognition output of a conversation to a concept marker and a verbalized version of a value associated with the concept marker based upon, at least in part, the automatic speech recognition output of the conversation. The concept marker and the verbalized version of the value associated with the concept marker may be replaced with a formatted version. A plurality of user selectable format configurations of the formatted version may be provided as a textual output in a user interface.

In some implementations, the instruction sets and subroutines of formatting process 10, which may be stored on storage device, such as storage device 16, coupled to computer 12, may be executed by one or more processors and one or more memory architectures included within computer 12. In some implementations, storage device 16 may include but is not limited to: a hard disk drive; all forms of flash memory storage devices; a tape drive; an optical drive; a RAID array (or other array); a random access memory (RAM); a read-only memory (ROM); or combination thereof. In some implementations, storage device 16 may be organized as an extent, an extent pool, a RAID extent (e.g., an example 4D+1P R5, where the RAID extent may include, e.g., five storage device extents that may be allocated from, e.g., five different storage devices), a mapped RAID (e.g., a collection of RAID extents), or combination thereof.

In some implementations, network 14 may be connected to one or more secondary networks (e.g., network 18), examples of which may include but are not limited to: a local area network; a wide area network or other telecommunications network facility; or an intranet, for example. The phrase "telecommunications network facility," as used herein, may refer to a facility configured to transmit, and/or receive transmissions to/from one or more mobile client electronic devices (e.g., cellphones, etc.) as well as many others.

In some implementations, computer 12 may include a data store, such as a database (e.g., relational database, object-oriented database, triplestore database, etc.) and may be located within any suitable memory location, such as storage device 16 coupled to computer 12. In some implementations, data, metadata, information, etc. described throughout the present disclosure may be stored in the data store. In some implementations, computer 12 may utilize any known database management system such as, but not limited to, DB2, in order to provide multi-user access to one or more databases, such as the above noted relational database. In some implementations, the data store may also be a custom database, such as, for example, a flat file database or an XML database. In some implementations, any other form(s) of a data storage structure and/or organization may also be used. In some implementations, formatting process 10 may be a component of the data store, a standalone application that interfaces with the above noted data store and/or an applet/application that is accessed via client applications 22, 24, 26, 28. In some implementations, the above noted data store may be, in whole or in part, distributed in a cloud computing topology. In this way, computer 12 and storage device 16 may refer to multiple devices, which may also be distributed throughout the network.

In some implementations, computer 12 may execute an automatic speech recognition application (e.g., automatic speech recognition application 20), examples of which may include, but are not limited to, e.g., an automatic speech recognition (ASR) application (e.g., speech recognition application 20), examples of which may include, but are not limited to, e.g., an automatic speech recognition (ASR) application (e.g., modeling, etc.), a natural language understanding (NLU) application (e.g., machine learning, intent discovery, etc.), a text to speech (TTS) application (e.g., context awareness, learning, etc.), a speech signal enhancement (SSE) application (e.g., multi-zone processing/beamforming, noise suppression, etc.), a voice biometrics/wake-up-word processing application, an automated clinical documentation (ACD) application, or other application that allows for ASR functionality. In some implementations, formatting process 10 and/or automatic speech recognition application 20 may be accessed via one or more of client applications 22, 24, 26, 28. In some implementations, formatting process 10 may be a standalone application, or may be an applet/application/script/extension that may interact with and/or be executed within automatic speech recognition application 20, a component of automatic speech recognition application 20, and/or one or more of client applications 22, 24, 26, 28. In some implementations, automatic speech recognition application 20 may be a standalone application, or may be an applet/application/script/extension that may interact with and/or be executed within formatting process 10, a component of formatting process 10, and/or one or more of client applications 22, 24, 26, 28. In some implementations, one or more of client applications 22, 24, 26, 28 may be a standalone application, or may be an applet/application/script/extension that may interact with and/or be executed within and/or be a component of formatting process 10 and/or automatic speech recognition application 20. Examples of client applications 22, 24, 26, 28 may include, but are not limited to, e.g., an automatic speech recognition (ASR) application (e.g., speech recognition application 20), examples of which may include, but are not limited to, e.g., an automatic speech recognition (ASR) application (e.g., modeling, etc.), a natural language understanding (NLU) application (e.g., machine learning, intent discovery, etc.), a text to speech (TTS) application (e.g., context awareness, learning, etc.), a speech signal enhancement (SSE) application (e.g., multi-zone processing/beamforming, noise suppression, etc.), a voice biometrics/wake-up-word processing application, an automated clinical documentation (ACD) application, or other application that allows for ASR functionality, a standard and/or mobile web browser, an email application (e.g., an email client application), a textual and/or a graphical user interface, a customized web browser, a plugin, an Application Programming Interface (API), or a custom application. The instruction sets and subroutines of client applications 22, 24, 26, 28, which may be stored on storage devices 30, 32, 34, 36, coupled to client electronic devices 38, 40, 42, 44, may be executed by one or more processors and one or more memory architectures incorporated into client electronic devices 38, 40, 42, 44.

In some implementations, one or more of storage devices 30, 32, 34, 36, may include but are not limited to: hard disk drives; flash drives, tape drives; optical drives; RAID arrays; random access memories (RAM); and read-only memories (ROM). Examples of client electronic devices 38, 40, 42, 44 (and/or computer 12) may include, but are not limited to, a personal computer (e.g., client electronic device 38), a laptop computer (e.g., client electronic device 40), a smart/data-enabled, cellular phone (e.g., client electronic device 42), a notebook computer (e.g., client electronic device 44), a tablet, a server, a television, a smart television, a smart speaker, an Internet of Things (IoT) device, a media (e.g., audio/video, photo, etc.) capturing and/or output device, an audio input and/or recording device (e.g., a handheld microphone, a lapel microphone, an embedded microphone (such as those embedded within eyeglasses, smart phones, tablet computers and/or watches, etc.), and a dedicated network device. Client electronic devices 38, 40, 42, 44 may each execute an operating system, examples of which may include but are not limited to, Android™, Apple® iOS®, Mac® OS X®; Red Hat® Linux®, Windows® Mobile, Chrome OS, Blackberry OS, Fire OS, or a custom operating system.

In some implementations, one or more of client applications 22, 24, 26, 28 may be configured to effectuate some or all of the functionality of formatting process 10 (and vice versa). Accordingly, in some implementations, formatting process 10 may be a purely server-side application, a purely client-side application, or a hybrid server-side/client-side application that is cooperatively executed by one or more of client applications 22, 24, 26, 28 and/or formatting process 10.

In some implementations, one or more of client applications 22, 24, 26, 28 may be configured to effectuate some or all of the functionality of automatic speech recognition application 20 (and vice versa). Accordingly, in some implementations, automatic speech recognition application 20 may be a purely server-side application, a purely client-side application, or a hybrid server-side/client-side application that is cooperatively executed by one or more of client applications 22, 24, 26, 28 and/or automatic speech recognition application 20. As one or more of client applications 22, 24, 26, 28, formatting process 10, and automatic speech recognition application 20, taken singly or in any combination, may effectuate some or all of the same functionality, any description of effectuating such functionality via one or more of client applications 22, 24, 26, 28, formatting process 10, automatic speech recognition application 20, or combination thereof, and any described interaction(s) between one or more of client applications 22, 24, 26, 28, formatting process 10, automatic speech recognition application 20, or combination thereof to effectuate such functionality, should be taken as an example only and not to limit the scope of the disclosure.

In some implementations, one or more of users 46, 48, 50, 52 may access computer 12 and formatting process 10 (e.g., using one or more of client electronic devices 38, 40, 42, 44) directly through network 14 or through secondary network 18. Further, computer 12 may be connected to network 14 through secondary network 18, as illustrated with phantom link line 54. Formatting process 10 may include one or more user interfaces, such as browsers and textual or graphical user interfaces, through which users 46, 48, 50, 52 may access formatting process 10.

In some implementations, the various client electronic devices may be directly or indirectly coupled to network 14 (or network 18). For example, client electronic device 38 is shown directly coupled to network 14 via a hardwired network connection. Further, client electronic device 44 is shown directly coupled to network 18 via a hardwired network connection. Client electronic device 40 is shown wirelessly coupled to network 14 via wireless communication channel 56 established between client electronic device 40 and wireless access point (i.e., WAP) 58, which is shown directly coupled to network 14. WAP 58 may be, for example, an IEEE 802.11a, 802.11b, 802.11g, 802.11n, 802.11ac, Wi-Fi®, RFID, and/or Bluetooth™ (including Bluetooth™ Low Energy) device that is capable of establishing wireless communication channel 56 between client electronic device 40 and WAP 58. Client electronic device 42 is shown wirelessly coupled to network 14 via wireless communication channel 60 established between client electronic device 42 and cellular network/bridge 62, which is shown by example directly coupled to network 14.

In some implementations, some or all of the IEEE 802.11x specifications may use Ethernet protocol and carrier sense multiple access with collision avoidance (i.e., CSMA/CA) for path sharing. The various 802.11x specifications may use phase-shift keying (i.e., PSK) modulation or complementary code keying (i.e., CCK) modulation, for example. Bluetooth™ (including Bluetooth™ Low Energy) is a telecommunications industry specification that allows, e.g., mobile phones, computers, smart phones, and other electronic devices to be interconnected using a short-range wireless connection. Other forms of interconnection (e.g., Near Field Communication (NFC)) may also be used.

In some implementations, various I/O requests (e.g., I/O request 15) may be sent from, e.g., client applications 22, 24, 26, 28 to, e.g., computer 12. Examples of I/O request 15 may include but are not limited to, data write requests (e.g., a request that content be written to computer 12) and data read requests (e.g., a request that content be read from computer 12).

Figure 2:
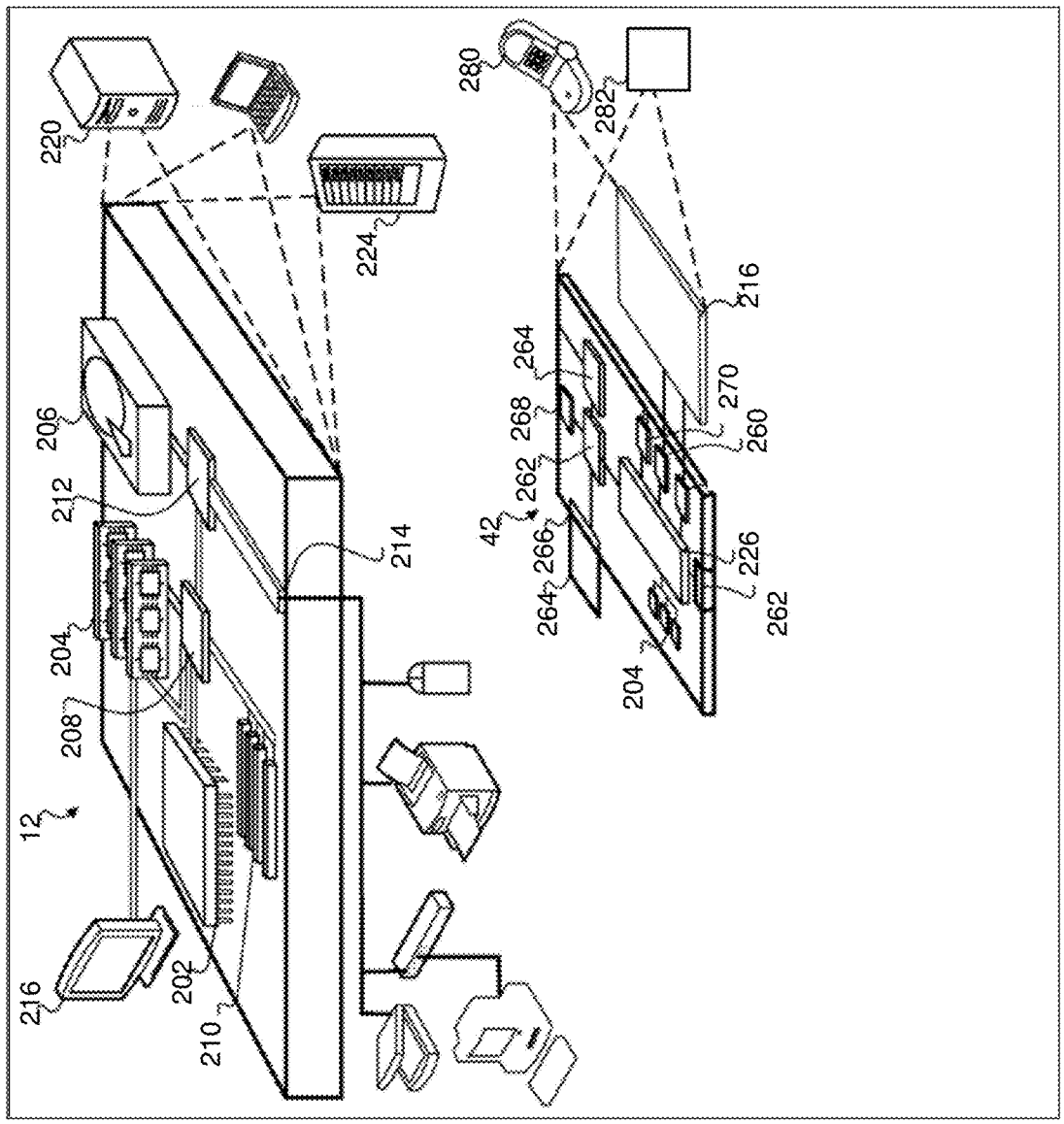
FIG. 2 is an example diagrammatic view of a computer and client electronic device of FIG. 1 according to one or more example implementations of the disclosure.
Figure 3:
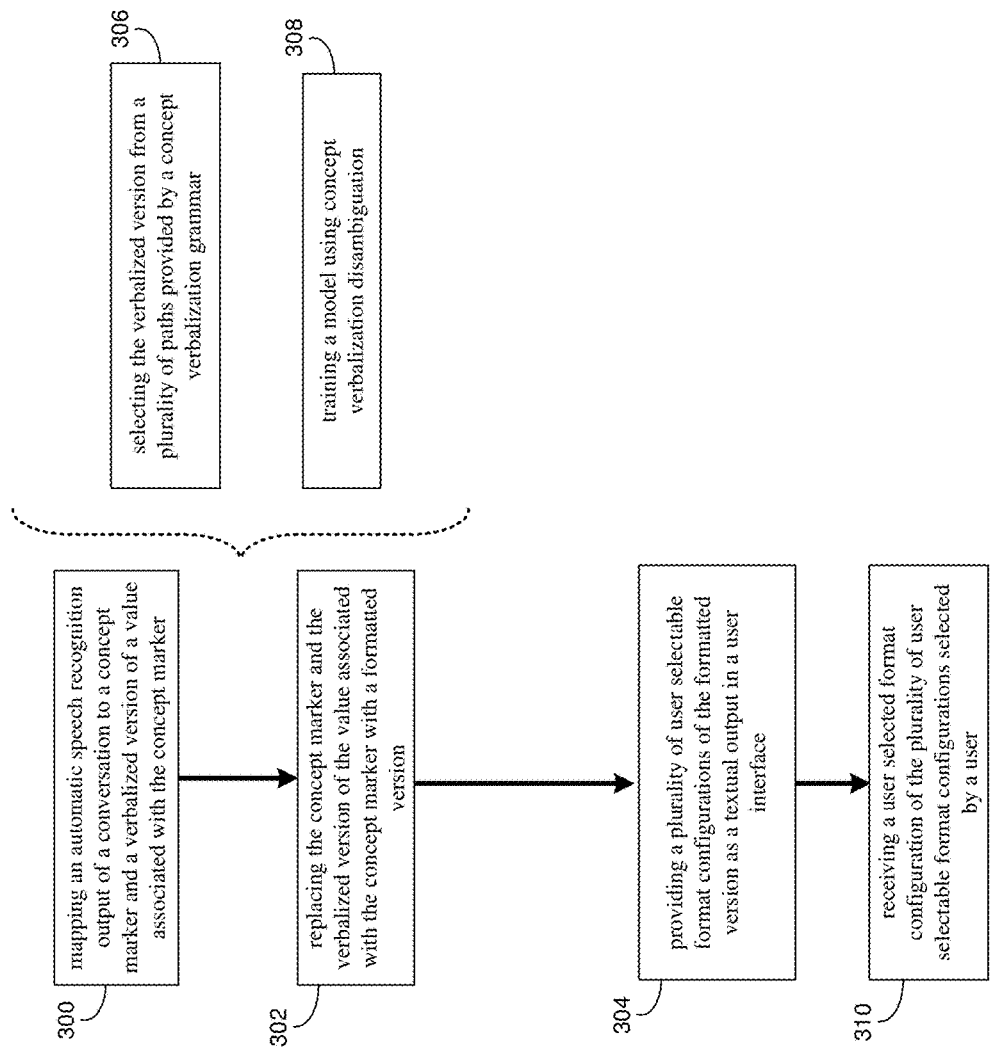
FIG. 3 is an example flowchart of a formatting process according to one or more example implementations of the disclosure.

Referring also to the example implementation of FIG. 2, there is shown a diagrammatic view of computer 12 and client electronic device 42. While client electronic device 42 and computer 12 are shown in this figure, this is for example purposes only and is not intended to be a limitation of this disclosure, as other configurations are possible. Additionally, any computing device capable of executing, in whole or in part, formatting process 10 may be substituted for client electronic device 42 and computer 12 (in whole or in part) within FIG. 2, examples of which may include but are not limited to one or more of client electronic devices 38, 40, and 44. Client electronic device 42 and/or computer 12 may also include other devices, such as televisions with one or more processors embedded therein or attached thereto as well as any of the microphones, microphone arrays, and/or speakers described herein. The components shown here, their connections and relationships, and their functions, are meant to be examples only, and are not meant to limit implementations of the disclosure described.

In some implementations, computer 12 may include processor 202, memory 204, storage device 206, a high-speed interface 208 connecting to memory 204 and high-speed expansion ports 210, and low speed interface 212 connecting to low speed bus 214 and storage device 206. Each of the components 202, 204, 206, 208, 210, and 212, may be interconnected using various busses, and may be mounted on a common motherboard or in other manners as appropriate. The processor 202 can process instructions for execution within the computer 12, including instructions stored in the memory 204 or on the storage device 206 to display graphical information for a GUI on an external input/output device, such as display 216 coupled to high speed interface 208. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

Memory 204 may store information within the computer 12. In one implementation, memory 204 may be a volatile memory unit or units. In another implementation, memory 204 may be a non-volatile memory unit or units. The memory 204 may also be another form of computer-readable medium, such as a magnetic or optical disk.

Storage device 206 may be capable of providing mass storage for computer 12. In one implementation, the storage device 206 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as the memory 204, the storage device 206, memory on processor 202, or a propagated signal.

High speed controller 208 may manage bandwidth-intensive operations for computer 12, while the low speed controller 212 may manage lower bandwidth-intensive operations. Such allocation of functions is exemplary only. In one implementation, the high-speed controller 208 may be coupled to memory 204, display 216 (e.g., through a graphics processor or accelerator), and to high-speed expansion ports 210, which may accept various expansion cards (not shown). In the implementation, low-speed controller 212 is coupled to storage device 206 and low-speed expansion port 214. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

Computer 12 may be implemented in a number of different forms, as shown in the figure. For example, computer 12 may be implemented as a standard server 220, or multiple times in a group of such servers. It may also be implemented as part of a rack server system 224. Alternatively, components from computer 12 may be combined with other components in a mobile device (not shown), such as client electronic device 42. Each of such devices may contain one or more of computer 12, client electronic device 42, and an entire system may be made up of multiple computing devices communicating with each other.

Client electronic device 42 may include processor 226, memory 204, an input/output device such as display 216, a communication interface 262, and a transceiver 264, among other components. Client electronic device 42 may also be provided with a storage device, such as a microdrive or other device, to provide additional storage. Each of the components 226, 204, 216, 262, and 264, may be interconnected using various buses, and several of the components may be mounted on a common motherboard or in other manners as appropriate.

Processor 226 may execute instructions within client electronic device 42, including instructions stored in the memory 204. The processor may be implemented as a chipset of chips that include separate and multiple analog and digital processors. The processor may provide, for example, for coordination of the other components of client electronic device 42, such as control of user interfaces, applications run by client electronic device 42, and wireless communication by client electronic device 42.

In some embodiments, processor 226 may communicate with a user through a control interface and display interface 260 coupled to a display 216. The display 216 may be, for example, a TFT LCD (Thin-Film-Transistor Liquid Crystal Display) or an OLED (Organic Light Emitting Diode) display, or other appropriate display technology. The display interface 260 may comprise appropriate circuitry for driving the display 216 to present graphical and other information to a user. The control interface may receive commands from a user and convert them for submission to the processor 226.

In addition, an external interface may be provide in communication with processor 226, so as to enable near area communication of client electronic device 42 with other devices. External interface 262 may provide, for example, for wired communication in some implementations, or for wireless communication in other implementations, and multiple interfaces may also be used.

In some embodiments, memory 204 may store information within the Client electronic device 42. The memory 204 can be implemented as one or more of a computer-readable medium or media, a volatile memory unit or units, or a non-volatile memory unit or units. Expansion memory may also be provided and connected to client electronic device 42 through expansion interface 266, which may include, for example, a SIMM (Single In Line Memory Module) card interface. Such expansion memory may provide extra storage space for client electronic device 42, or may also store applications or other information for client electronic device 42. Specifically, expansion memory may include instructions to carry out or supplement the processes described above, and may include secure information also. Thus, for example, expansion memory may be provide as a security module for client electronic device 42, and may be programmed with instructions that permit secure use of client electronic device 42. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product may contain instructions that, when executed, perform one or more methods, such as those described above. The information carrier may be a computer- or machine-readable medium, such as the memory 204, expansion memory, memory on processor 226, or a propagated signal that may be received, for example, over transceiver 264 or external interface.

Client electronic device 42 may communicate wirelessly through communication interface 262, which may include digital signal processing circuitry where necessary. Communication interface 262 may provide for communications under various modes or protocols, such as GSM voice calls, SMS, EMS, or MMS speech recognition, CDMA, TDMA, PDC, WCDMA, CDMA2000, or GPRS, among others. Such communication may occur, for example, through radio-frequency transceiver 264. In addition, short-range communication may occur, such as using a Bluetooth, WiFi, or other such transceiver (not shown). In addition, GPS (Global Positioning System) receiver module 268 may provide additional navigation and location-related wireless data to client electronic device 42, which may be used as appropriate by applications running on client electronic device 42.

Client electronic device 42 may also communicate audibly using audio codec 270, which may receive spoken information from a user and convert it to usable digital information. Audio codec 270 may likewise generate audible sound for a user, such as through a speaker, e.g., in a handset of client electronic device 42. Such sound may include sound from voice telephone calls, may include recorded sound (e.g., voice messages, music files, etc.) and may also include sound generated by applications operating on client electronic device 42.

Client electronic device 42 may be implemented in a number of different forms, as shown in the figure. For example, it may be implemented as a cellular telephone 280. It may also be implemented as part of a smartphone 282, personal digital assistant, remote control, or other similar mobile device.

Automated Clinical Documentation (ACD) may be used, e.g., to turn transcribed conversational (e.g., physician-patient) speech into formatted (e.g., medical) reports. In some implementations, the "heart" of the process may be sequence-to-sequence ("seq2seq") models, which transform the ASR output to a final report. In current systems, different examples of various concepts (such as dates, vital signs and dosage) are "rendered" by the seq2seq model. That is, the model must typically learn the way the concepts are formatted. This may result in multiple example disadvantages. For example, if an institution has its own standards for formatting particular concepts (or changes those standards), the model must typically be retrained with data using these formatting rules, which takes time and resources. As another example, data from institutions with different formatting for these concepts cannot generally be maximally shared in training the seq2seq model. As yet another example, the seq2seq model generally has to use some of its capacity learning the output formatting (e.g., the mapping of how numeric expressions are verbalized vs. formatted). Therefore, as will be discussed below in greater detail, the present disclosure may make modifications to a typical seq2seq based ACD workflow to create an ACD system that allows an institution (or even individual doctors or other healthcare professionals) to specify and change concept formatting rules (e.g., semantic items like time, date, blood pressure, temperature, and other concepts that are primarily expressed as number) without one or more of the above-noted disadvantages.

As will be discussed below, formatting process 10 may at least help, e.g., improve existing technology, necessarily rooted in computer technology in order to overcome an example and non-limiting problem specifically arising in the realm of ASR systems associated with, e.g., being integrated into the practical application of ASR based concept formatting. It will be appreciated that the computer processes described throughout are integrated into one or more practical applications, and when taken at least as a whole are not considered to be well-understood, routine, and conventional functions.

The Formatting Process:

As discussed above and referring also at least to the example implementations of FIGS. 3-9, formatting process 10 may map 300, by a computing device an automatic speech recognition output of a conversation to a concept marker and a verbalized version of a value associated with the concept marker based upon, at least in part, the automatic speech recognition output of the conversation. Formatting process 10 may replace 302 the concept marker and the verbalized version of the value associated with the concept marker with a formatted version. Formatting process 10 may provide 304 a plurality of user selectable format configurations of the formatted version as a textual output in a user interface.

As will be discussed below, users of an Automated Clinical Documentation (ACD) system (e.g., doctors or other healthcare professionals and institutions) may want to control the formatting of various concepts and render them differently from each other. In some implementations, formatting process 10 may decompose the learning of the concept identification and value from the formatting (rendering) process so that an ACD learner (which may include portions of formatting process 10) may make the best use of data with potentially distinct formatting preferences across doctors (or other healthcare professionals) and institutions (e.g., for improved data efficiency) and the doctor (or institution) may configure the formatting decision without requiring the ACD learner to be adapted (e.g., for immediate formatting configurability). In some implementations, unlike formatting process 10, if a system were to require the ACD learner to directly map to formatted text, as a result, the ACD learner may need to learn and encode the mapping of verbalized concept sequences (e.g., one hundred ten over seventy) to formatted sequences (e.g., 110/70), which may unnecessarily erode data efficiency and likely increasing the number of errors in the ACD output.

In some implementations, formatting process 10 may map 300, by a computing device an automatic speech recognition output of a conversation to a concept marker and a verbalized version of a value associated with the concept marker based upon, at least in part, the automatic speech recognition output of the conversation. For example, formatting process 10 may map 300 from the automatic speech recognition (ASR) output of a conversation, which will typically include concepts that require configurable formatting. In the example, formatting process 10 may effect this by, e.g., first mapping 300 the ASR output, where instead of formatted concept values there are concept markers with verbalized versions of the values, and then (as will be discussed below), formatting process 10 may replace 302 the markers and verbalized values by their formatted version per grammars with configurable options. For instance, assume for example purposes only that a doctor (e.g., user 50) is with a patient using an ACD system associated with formatting process 10. In the example, further assume that with a doctor/patient consult transcript, the temperature of the patient is discussed, which may be received by an audio receiving feature (e.g., microphone) of any of the above-noted computing devices (e.g., client electronic device 42). For instance, the temperature documented in the report (which is inferred from the patient stating they have a fever of "a hundred and one"). This may be formatted as, e.g., "101°" but a particular doctor (e.g., user 50) or facility may prefer a format of, e.g., "101° F." or "101° F." or even "38° C.". As will be discussed below, it may be desirable (for formatting process 10) to support this level of configurability without a model having to learn from data alone to map, e.g., "a hundred and one" yielding "38° C.," since learning such a mapping may require many examples (e.g., of doctor-patient consult transcripts with temperatures and medical reports formatted with ° C., etc.). Further, it may be desirable (for formatting process 10) to allow a user/facility to revisit these decisions and not have to wait for a model to adapt to this change by learning from a doctor or scribe modifying the system output over and over again in reports. Additionally, it may be desirable (for formatting process 10) to allow the model to make better use of data across different doctors/facilities/scribes that happen to prefer to format numeric expressions in different ways (i.e., not unnecessarily fragment the training data). As a result, formatting process 10 may decompose the modeling of these concepts and the rendering of these concepts. Formatting process 10 may let the model learn from data to identify the concept and its value, which may be rendered using an expertly created (formatting/rendering) grammar that supports a user specifying their formatting preference (which may thus instantly be obliged), e.g., the doctor prefers temperatures with "° C." (as selected from a finite list of options supported by the grammar).

Figure 4:
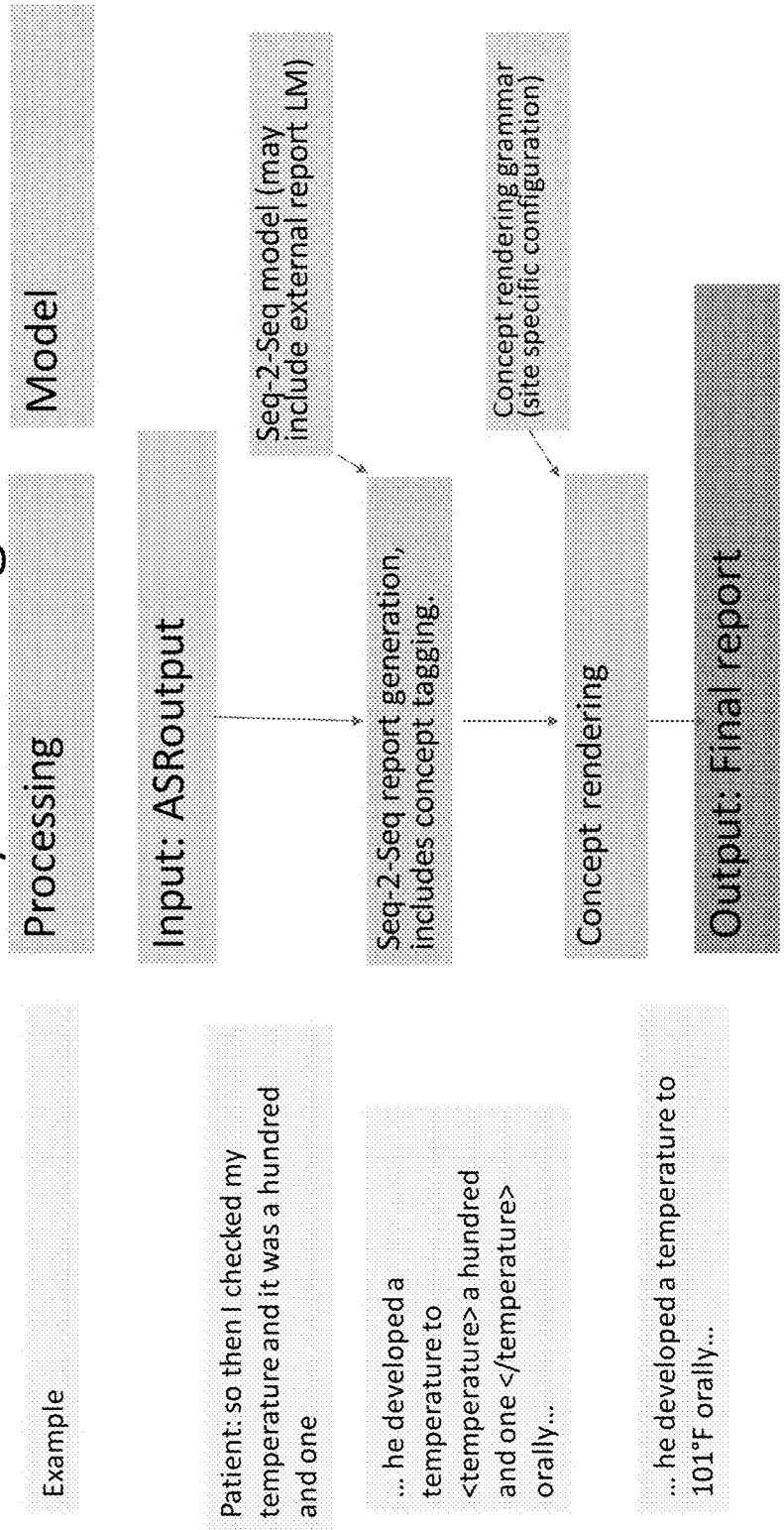
FIG. 4 is an example runtime system diagram of a formatting process according to one or more example implementations of the disclosure.
Figure 6:
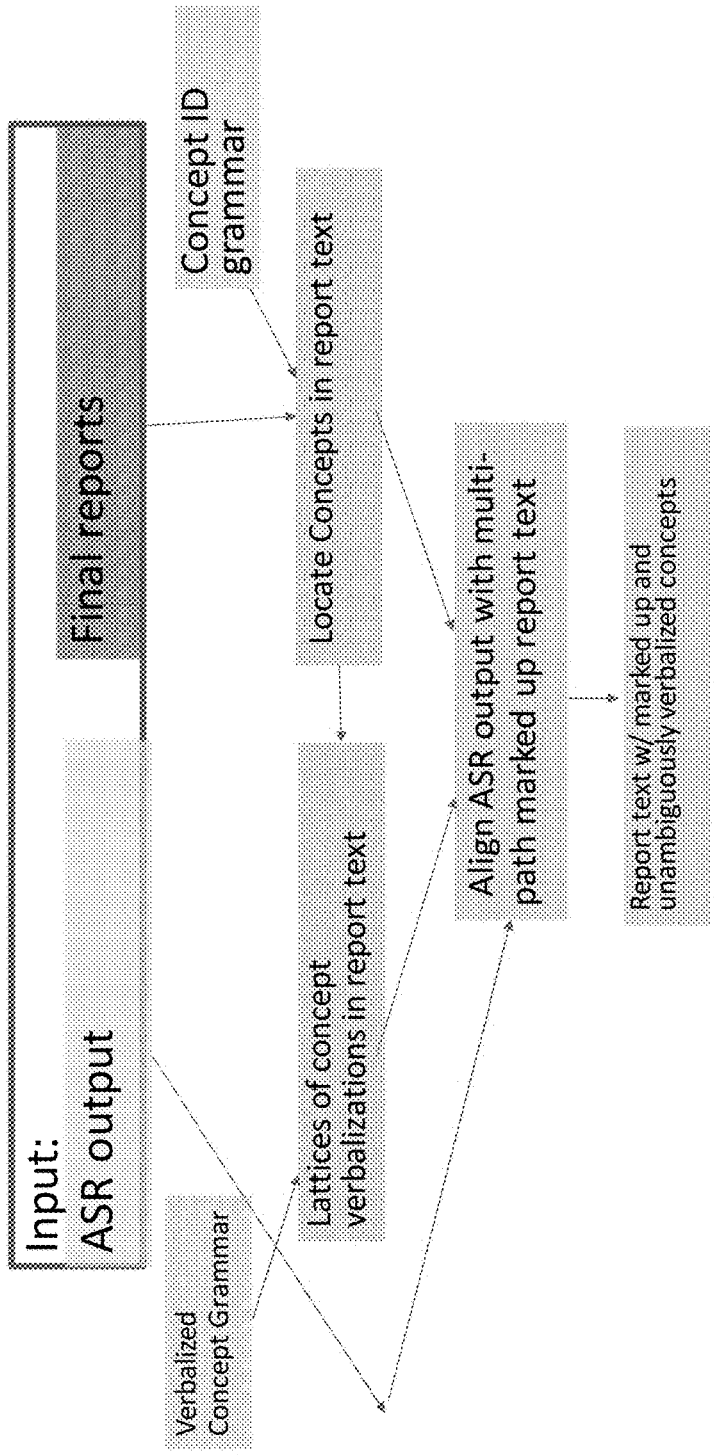
FIG. 6 is an example concept verbalization disambiguation diagram of a formatting process according to one or more example implementations of the disclosure.
Figure 8:
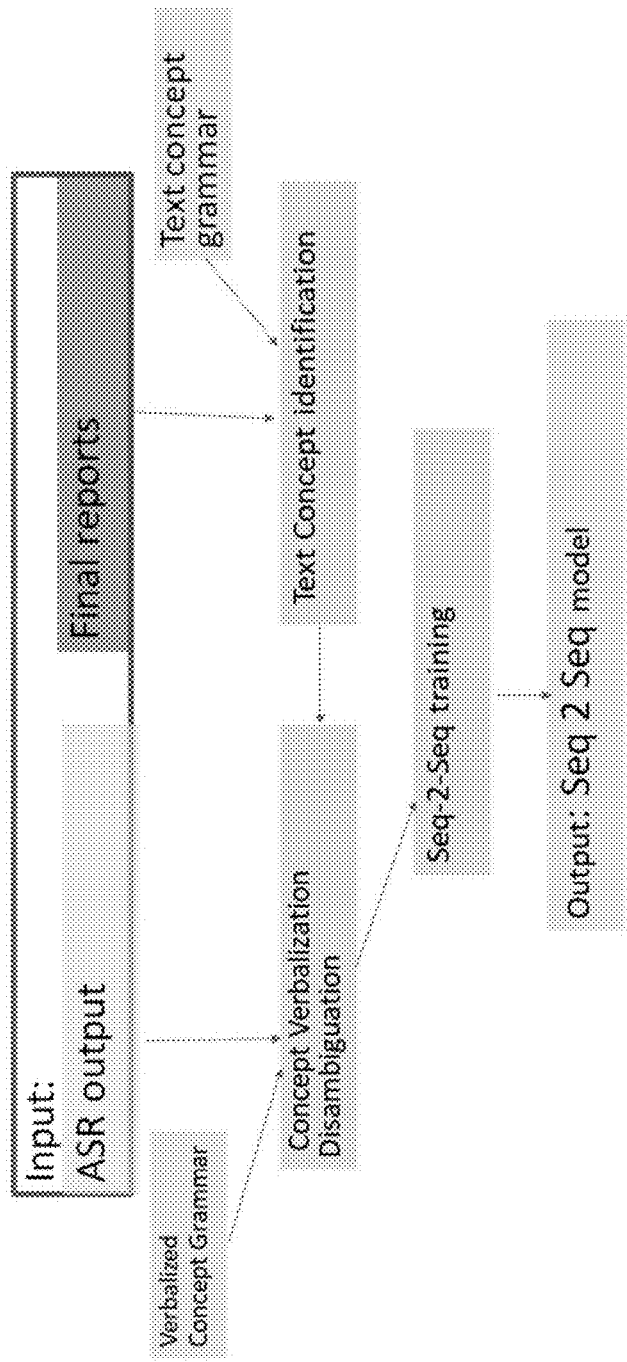
FIG. 8 is an example model training diagram of a formatting process according to one or more example implementations of the disclosure.
Figure 9:
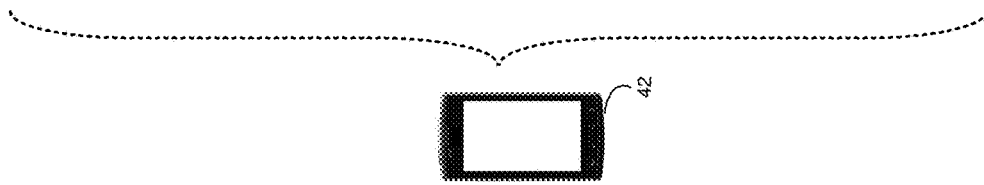
FIG. 9 is an example graphical user interface of a formatting process according to one or more example implementations of the disclosure.

Referring at least to the example implementation of FIG. 4 and FIG. 5, an example runtime system diagram 400 and runtime example 500 of formatting process 10 are shown. In the example, the concept of "temperature" and the verbalized version of a value associated with the concept marker (e.g., a hundred and one) may be based upon, at least in part, the automatic speech recognition output of the conversation to the medical report. As can be seen at least from FIG. 4 and FIG. 5, while some systems may decompose this statement with the resulting doctor dictation as the input, formatting process 10 may decompose this statement with the ASR output as the input.

In some implementations, formatting process 10 may replace 302 the concept marker and the verbalized version of the value associated with the concept marker with a formatted version. Replacing 302 the concept marker and the verbalized version of the value associated with the concept marker with the formatted version may occur as part of the runtime process. During the training process, rather than use an already formatted medical report text as the target for the learner (e.g., a sequence-to-sequence/seq2seq based neural network), formatting process may replace the formatted version (e.g., 101° F.) of the value associated with a concept marker (e.g., <temperature> . . . </temperature>) with a verbalized version (e.g. <temperature> a hundred and one </temperature>), which (to minimize the complexity of the learning task may be the simplest for the learner given the ASR output (e.g., reflecting the physician-patient consult transcript) or audio from which it is mapping. As such, formatting process 10 may modify the output target of a model (e.g., a seq2seq model) to include the concept markup, but verbalized rather than formatted values. Thus, a question may then be what exactly to use as the model's target output, which captures the concept identification and value such that the mapping is as easy as possible for the model. In some implementations, to minimize the amount of data, it may be required to train the model to perform well (discussed further below).

In some implementations, a concept identification grammar may be applied to the textual output of the medical report. For example, the concept identification (ID) grammar may be applied in the data preparation phase for model training and it may be applied to the formatted report. For example, in order to target anything beyond the exact rendering in the report (e.g., ". . . he developed a temperature to 101° F. orally . . . " in this example) formatting process 10 may need to identify the above-noted relevant numeric concept of "temperature" in the (formatted) report. In some implementations, this may be done via a rule-based mechanism (i.e., concept identification grammar), which may be expert created rather than learned from data. In some implementations, this grammar may also be able to identify and parse out the value, e.g., ". . . a temperature to <temperature>101° F.</temperature>orally . . . ".

In some implementations, formatting process 10 may select 306 the verbalized version from a plurality of paths provided by a concept verbalization grammar. For example, the medical report available to use for training may have fully formatted concepts, since that is what scribes/doctors may ultimately produce. The concept identification grammar may be applied to this formatted report and it may mark up formatted concepts with a concept identifier. For example, in some implementations, a path of the plurality of paths may be selected 306 based upon, at least in part, an edit distance alignment between the automatic speech recognition output and an associated target graph. For instance, an expertly crafted concept verbalization grammar may take (e.g., via formatting process 10) a formatted value for a concept like "101° F." for temperature and may create a lattice of all ways it knows it may be spoken, e.g., ((one oh one|a hundred and one|one hundred one| . . . ) [Fahrenheit]|thirty eight [Celsius]). Note that it may actually have been spoken in a novel way or simply partially misrecognized. At this point, formatting process 10 may have a network (e.g., directed acyclic graph or target graph) of possible targets for the model, e.g., "SUBJECTIVE he developed a temperature of <temperature>((one oh one|a hundred and one|one hundred one| . . . ) [Fahrenheit]|thirty eight [Celsius])</temperature> . . . ". This temperature is likely not the only formatted concept in the report. The simplest attempt at selecting 306 an "easy to model" path through this target graph/network may be for formatting process 10 to perform an edit distance alignment 700 (shown in the example implementation of FIG. 7) between the ASR ("Hi Brian I am Doctor Jones . . . ") and the associated directed acyclic graph. Based upon the directed acyclic graph, formatting process 10 may select a path with a minimum edit distance from the ASR input (as an intuitive measure of "easiest to model"). The process of going from a graph of possible targets for an input to a single target may be referred to as concept verbalization disambiguation 600 (shown in the example implementation of FIG. 6).

In some implementations, and continuing with the above example, formatting process 10 may train 308 a model using concept verbalization disambiguation. In some implementations, the model may be a sequence-to-sequence (seq2seq) model. The concept verbalization grammar may replace the formatted concept value with a plurality of verbalized value paths, which then may be selected based on edit distance alignment with the ASR transcript. For instance, an example 800 training of a seq2seq model is shown in the example implementation of FIG. 8. Once formatting process 10 has an unambiguous target for each input, formatting process 10 may train 308 the model (e.g., seq2seq) model. Given a trained model (possibly not all the way to convergence), formatting process 10 may refine the targets based on a more rigorous notion of "easiest to model" and may re-train (possibly from the previous starting point) with the hope of arriving at a better final model. For instance, in the example, the patient may also say "one oh one" at one point and while an edit distance calculation may effectively align that phrase with the temperature in the report (graph), it may actually be the latter "a hundred and one" that is responsible for it and may make for an easier/better target-). Specifically, formatting process 10 may use the trained model (which now may be reasonably good at predicting reports based on conversation transcripts) to indicate which target path is easiest, specifically to which the path formatting process 10 assigns maximal likelihood (i.e., determines is most probable). Generally, it may not be practical to enumerate all paths in the target graph and have the model assign likelihoods to them individually. Instead, in some implementations, formatting process 10 may perform a constrained beam search where formatting process 10 propagates a maximum of n model partial hypotheses that are all consistent with the target graph (e.g., they are all partial paths from the start of the graph, "SUBJECTIVE he developed . . . " in this example), extend each hypothesis by all valid tokens according to the graph, and retain the most likely (according to the model) up to a max of n.

In some implementations, to provide a less biased estimate, formatting process 10 may perform k-fold cross-validation, e.g., with k=2 the training corpus may be split in half, train a model from each half, and use the model from one half to choose the maximum likelihood target paths for the transcript-report pairs for the other half. Once there are updated/refined targets, formatting process 10 may retrain the model. In principle, formatting process 10 may iterate, using these better models (due to better/easier targets) to choose new targets for the basis of training. However, this may quickly converge, i.e. there is no change in the selected target paths from one iteration to the next (and so modulo randomization in the training process obtains the same model).

In some implementations, formatting process 10 may provide 304 a plurality of user selectable format configurations of the formatted version as a textual output of a user interface. For example, in the actual run time system, the seq2seq model may be applied to the ASR output, which may provide the report with the concept marker and verbalized values encoded therein and then a formatting grammar may be applied to complete the rendering. For example, as noted above, doctors (or other healthcare professionals or institutions) may want the ability to have dynamic formatting control and the ACD learner (via formatting process 10) may need to deal with diversity of formatting realities. For example, and referring at least to the example implementation of FIG. 9, an example graphical user interface (GUI) 900 is shown. In some implementations, this (formatting configurability) may be enabled using GUI 900 associated with formatting process 10. For example, at run-time, the actual formatting of concepts and values output by formatting process 10 may be accomplished (as described above), where the target outputs are exposed to the user. Thus, in the example, user 50 may be presented with the final transcribed report of the examination (e.g., based on the use of the ACD system), and may be further provided with the option to choose from multiple different formatting configurations that the concept (temperature) is presented on the report. For example, the portion of the report referring to the temperature may include a drop down menu 902 (or other type of selection method) that may include the multiple different formatting configurations of temperature that user 50 may select. It will be appreciated that while it may be possible to allow the doctor to change their mind per concept value in a given report, and choose an alternative, formatting process 10 may also support doctors, independent of a particular report, indicating their formatting preferences per concept (e.g., temperature, blood pressure, etc.) That is, GUI 900, instead of being a report, may include a window (or other object) that enables the doctor, institution, etc. to select their desired formatting preferences, which may be retained and used for all such concept rendering in all reports until/unless they were later adjusted. It will also be appreciated that other configurations of GUI 900 as well as other types of GUIs may be used with formatting process 10. As such, the use of GUI 900 should be taken as example only and not to otherwise limit the scope of the disclosure.

In some implementations, the default configurations for the concept formatting grammars may be induced by applying the concept identification grammar to data from the physician or institution and simply noting the maximally frequent rendering choices. For instance, if the institution frequently (e.g., a majority of the time or beyond a threshold number of times) selects "101°" as the formatting for temperature, this format may be originally provided in the final report (or field of the final report), which may then be changed by the user by selecting their preferred formatting (e.g., via the above-noted drop down menu). In some implementations, the default options may be, e.g., set per clinic, and the doctors (or otherwise) may adjust similarly as described above.

In some implementations, formatting process 10 may receive 310 a user selected format configuration of the plurality of user selectable format configurations selected by a user. For instance, and continuing with the above example, since user 50 has selected the format of 101° F. instead of 101°, formatting process 10 may receive 310 the user selected format at runtime for the concept formatting/rendering grammars. As such, in some implementations, the next time temperature is presented in a report (or elsewhere for documentation by user 50) and identified using the concept marker, formatting process 10 may present the output of the report text (or other abstractive summarization) in the selected format of 101°F.

Accordingly, formatting process 10 may use models (e.g., seq2seq models or other similar models) for abstractive summarization, and in particular may modify the data preparation and decompose the inference process to allow easy (and dynamic) customization for formatting concepts. Additionally, rather than using, e.g., a physician-patient conversation as the input to the mapping task, formatting process 10 may use the ASR output (e.g., from the physician dictation or speech) as the input to the mapping task, as well as use determination of the target for the mapper learned from data (e.g., concept verbalization disambiguation (CVD)).

It will be appreciated that while the present disclosure may be described in terms of an ACD system, other non-medical systems may benefit from the use of formatting process 10. As such, the use of an ACD (or other medical type system) should be taken as example only and not to otherwise limit the scope of the disclosure. Similarly, it will be appreciated that concepts other than temperature may be used without departing from the scope of the disclosure. As such, the use of temperature as the concept should be taken as example only and not to otherwise limit the scope of the disclosure.

The terminology used herein is for the purpose of describing particular implementations only and is not intended to be limiting of the disclosure. As used herein, the singular forms "a", "an" and "the" are intended to include the plural forms as well, unless the context clearly indicates otherwise. As used herein, the language "at least one of A, B, and C" (and the like) should be interpreted as covering only A, only B, only C, or any combination of the three, unless the context clearly indicates otherwise. It will be further understood that the terms "comprises" and/or "comprising," when used in this specification, specify the presence of stated features, integers, steps (not necessarily in a particular order), operations, elements, and/or components, but do not preclude the presence or addition of one or more other features, integers, steps (not necessarily in a particular order), operations, elements, components, and/or groups thereof.

The corresponding structures, materials, acts, and equivalents (e.g., of all means or step plus function elements) that may be in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications, variations, substitutions, and any combinations thereof will be apparent to those of ordinary skill in the art without departing from the scope and spirit of the disclosure. The implementation(s) were chosen and described in order to explain the principles of the disclosure and the practical application, and to enable others of ordinary skill in the art to understand the disclosure for various implementation(s) with various modifications and/or any combinations of implementation(s) as are suited to the particular use contemplated.

Having thus described the disclosure of the present application in detail and by reference to implementation(s) thereof, it will be apparent that modifications, variations, and any combinations of implementation(s) (including any modifications, variations, substitutions, and combinations thereof) are possible without departing from the scope of the disclosure defined in the appended claims.

What is claimed is:

1. A computer-implemented method comprising:
    mapping, by a computing device, an automatic speech recognition output of a conversation to a concept marker and a verbalized version of a numerical value associated with the concept marker based upon, at least in part, the automatic speech recognition output of the conversation;
    replacing the concept marker and the verbalized version of the numerical value associated with the concept marker with a formatted numerical version;
    providing a plurality of user selectable format configurations of the formatted numerical version as a textual output in a user interface;
    receiving a user selected format configuration of the plurality of user selectable format configurations of the formatted numerical version selected by a user in the user interface, wherein a concept identification grammar is applied to the textual output of a transcribed medical report based upon the user selected format configuration; and
    altering the textual output of the transcribed medical report to correspond to the user selected format configuration of the plurality of user selectable format configurations of the formatted numerical version selected by the user in the user interface and altering, as a default setting, the textual output in other documentation to correspond to the user selected format configuration of the plurality of user selectable format configurations of the formatted numerical version selected by the user in the user interface based upon, at least in part, a number of times the user and one or more additional users select the user selected format configuration of the plurality of user selectable format configurations of the formatted numerical version compared to a number of times the user and one or more additional users select a different user selected format configuration of the plurality of user selectable format configurations of the formatted numerical version.

2. The computer-implemented method of claim 1 further comprising selecting the verbalized version from a plurality of paths provided by a concept verbalization grammar.

3. The computer-implemented method of claim 2 wherein a path of the plurality of paths is selected based upon, at least in part, an edit distance alignment between the automatic speech recognition output and an associated target graph.

4. The computer-implemented method of claim 1 further comprising training a model using concept verbalization disambiguation.

5. The computer-implemented method of claim 4 wherein the model is a sequence-to-sequence model.

6. A computer program product residing on a non-transitory computer readable storage medium having a plurality of instructions stored thereon which, when executed across one or more processors, causes at least a portion of the one or more processors to perform operations comprising:
    mapping an automatic speech recognition output of a conversation to a concept marker and a verbalized version of a numerical value associated with the concept marker based upon, at least in part, the automatic speech recognition output of the conversation;

replacing the concept marker and the verbalized version of the numerical value associated with the concept marker with a formatted numerical version;

providing a plurality of user selectable format configurations of the formatted numerical version as a textual output in a user interface;

receiving a user selected format configuration of the plurality of user selectable format configurations of the formatted numerical version selected by a user in the user interface, wherein a concept identification grammar is applied to the textual output of a transcribed medical report based upon the user selected format configuration; and altering the textual output of the transcribed medical report to correspond to the user selected format configuration of the plurality of user selectable format configurations of the formatted numerical version selected by the user in the user interface and altering, as a default setting, the textual output in other documentation to correspond to the user selected format configuration of the plurality of user selectable format configurations of the formatted numerical version selected by the user in the user interface based upon, at least in part, a number of times the user and one or more additional users select the user selected format configuration of the plurality of user selectable format configurations of the formatted numerical version compared to a number of times the user and one or more additional users select a different user selected format configuration of the plurality of user selectable format configurations of the formatted numerical version.

7. The computer program product of claim 6 wherein the operations further comprise selecting the verbalized version from a plurality of paths provided by a concept verbalization grammar.

8. The computer program product of claim 7 wherein a path of the plurality of paths is selected based upon, at least in part, an edit distance alignment between the automatic speech recognition output and an associated target graph.

9. The computer program product of claim 6 wherein the instructions further comprise training a model using concept verbalization disambiguation.

10. The computer program product of claim 9 wherein the model is a sequence-to-sequence model.

11. A computing system including one or more processors and one or more memories configured to perform operations comprising:

mapping an automatic speech recognition output of a conversation to a concept marker and a verbalized version of a numerical value associated with the concept marker based upon, at least in part, the automatic speech recognition output of the conversation;

replacing the concept marker and the verbalized version of the numerical value associated with the concept marker with a formatted numerical version;

providing a plurality of user selectable format configurations of the formatted numerical version as a textual output in a user interface;

receiving a user selected format configuration of the plurality of user selectable format configurations of the formatted numerical version selected by a user in the user interface, wherein a concept identification grammar is applied to the textual output of a transcribed medical report based upon the user selected format configuration; and altering the textual output of the transcribed medical report to correspond to the user selected format configuration of the plurality of user selectable format configurations of the formatted numerical version selected by the user in the user interface and altering, as a default setting, the textual output in other documentation to correspond to the user selected format configuration of the plurality of user selectable format configurations of the formatted numerical version selected by the user in the user interface based upon, at least in part, a number of times the user and one or more additional users select the user selected format configuration of the plurality of user selectable format configurations of the formatted numerical version compared to a number of times the user and one or more additional users select a different user selected format configuration of the plurality of user selectable format configurations of the formatted numerical version.

12. The computing system of claim 11 wherein the operations further comprise selecting the verbalized version from a plurality of paths provided by a concept verbalization grammar.

13. The computing system of claim 12 wherein a path of the plurality of paths is selected based upon, at least in part, an edit distance alignment between the automatic speech recognition output and an associated target graph.

14. The computing system of claim 11 wherein the instructions further comprise training a model using concept verbalization disambiguation.

15. The computer-implemented method of claim 1 wherein the concept marker and the formatted numerical version are associated with one of temperature and blood pressure.

* * * * *